United States Patent

Ando et al.

[11] Patent Number: 5,235,275
[45] Date of Patent: Aug. 10, 1993

[54] MAGNETIC INSPECTION APPARATUS FOR THIN STEEL STRIP HAVING MAGNETIZER AND DETECTION COIL WITHIN A HOLLOW ROLLER ROTATED BY THE STEEL STRIP

[75] Inventors: Seigo Ando; Masaki Takenaka; Kenichi Iwanaga; Takato Furukawa; Atsuhisa Takekoshi, all of Tokyo, Japan

[73] Assignee: NKK Corporation, Tokyo, Japan

[21] Appl. No.: 768,986
[22] PCT Filed: Feb. 22, 1991
[86] PCT No.: PCT/JP91/00224
  § 371 Date: Oct. 17, 1991
  § 102(e) Date: Oct. 17, 1991
[87] PCT Pub. No.: WO91/13347
  PCT Pub. Date: Sep. 5, 1991

[30] Foreign Application Priority Data

| Feb. 22, 1990 | [JP] | Japan | 2-41840 |
| Mar. 9, 1990 | [JP] | Japan | 2-23250[U] |
| Mar. 27, 1990 | [JP] | Japan | 2-77379 |
| Jul. 19, 1990 | [JP] | Japan | 2-189484 |
| Jul. 27, 1990 | [JP] | Japan | 2-197871 |
| Oct. 19, 1990 | [JP] | Japan | 2-278918 |

[51] Int. Cl.$^5$ ............ G01N 27/83; G01R 33/04; G01R 33/12
[52] U.S. Cl. .................... 324/238; 324/242; 324/255; 324/261; 324/262
[58] Field of Search ........ 324/206, 226, 227, 229-231, 324/235, 239-243, 261, 262; 73/159; 340/675, 676; 72/10, 11, 16

[56] References Cited

U.S. PATENT DOCUMENTS

| 2,938,164 | 5/1960 | Hansburg | 324/255 |
| 3,662,576 | 5/1972 | Girlatschek . | |
| 3,748,575 | 7/1973 | Lapper . | |
| 3,781,662 | 12/1973 | Davis . | |
| 3,886,445 | 5/1975 | Chiba et al. . | |
| 4,107,606 | 8/1978 | Typpo et al. | 324/229 |
| 4,305,035 | 12/1981 | Mach et al. | 324/255 |
| 4,518,919 | 5/1985 | Ishida | 324/228 |
| 4,519,249 | 5/1985 | Hunt | 73/596 |
| 4,767,987 | 8/1988 | Montgomery | 324/231 |
| 5,089,776 | 2/1992 | Furukawa et al. | 324/262 X |

FOREIGN PATENT DOCUMENTS

| 2620070 | 5/1976 | Fed. Rep. of Germany . |
| 2310566 | 3/1976 | France . |
| 57-108656 | 7/1982 | Japan . |
| 61-170067 | 10/1986 | Japan . |
| 61-170068 | 10/1986 | Japan . |
| 62-111539 | 7/1987 | Japan . |
| 63-96547 | 4/1988 | Japan . |
| 63-107849 | 7/1988 | Japan . |
| 1-308982 | 12/1989 | Japan . |
| 1311907 | 3/1973 | United Kingdom . |

OTHER PUBLICATIONS

Patent Abstracts of Japan, vol. 10, No. 344, Nov. 20, 1986, Nippon Steel Corp., Defect Detecting Device for Strip.

Primary Examiner—Gerard R. Strecker
Attorney, Agent, or Firm—Frishauf, Holtz, Goodman & Woodward

[57] ABSTRACT

In a magnetic inspection apparatus for a thin steel strip of the invention, a pole-to-pole distance of a magnetizer, which is housed in a hollow roller contacting a traveling thin steel strip to oppose the thin steel strip, is set between twice and eight times a distance between magnetic poles and the thin steel strip. A position of a magnetic sensor in the travel direction of the thin steel strip is shifted from the central position of the magnetic poles to a travel direction side by a small distance. In this invention, a pair of hollow rollers are provided to sandwich upper and lower surfaces of a traveling thin steel strip, and magnetic sensors are respectively housed in the hollow rollers. As a result, a position of a defect in the direction of the thickness of the thin steel strip, and a defect size can be accurately detected. In a magnetic inspection apparatus for a thin steel strip of the invention, a magnetic detection circuit for detecting magnetic flux leakage caused by a defect in the interior or on the surface of a thin steel strip uses an over-saturation type magnetic sensor constituted by applying a detection coil around a ferromagnetic core. As a result, a defect detection sensibility and a defect detection precision are greatly improved.

3 Claims, 17 Drawing Sheets

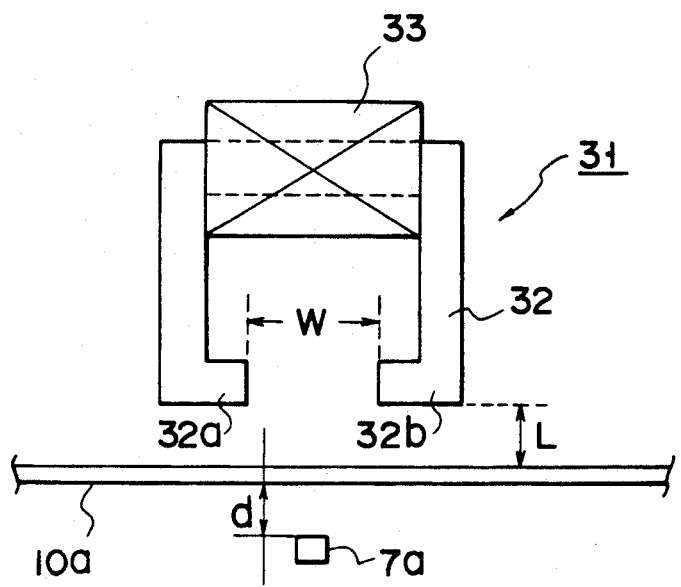
F I G. 3

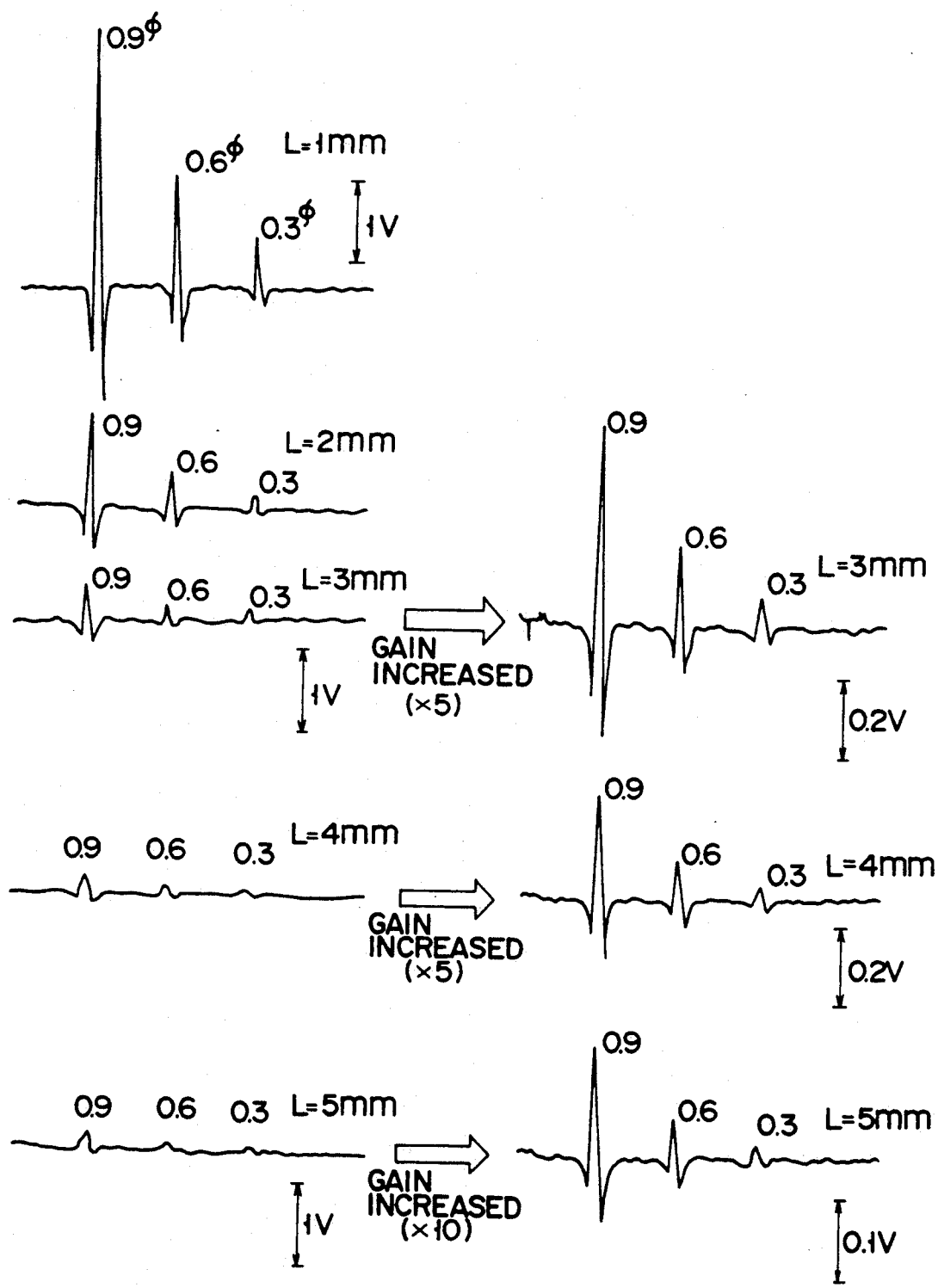
F I G. 6

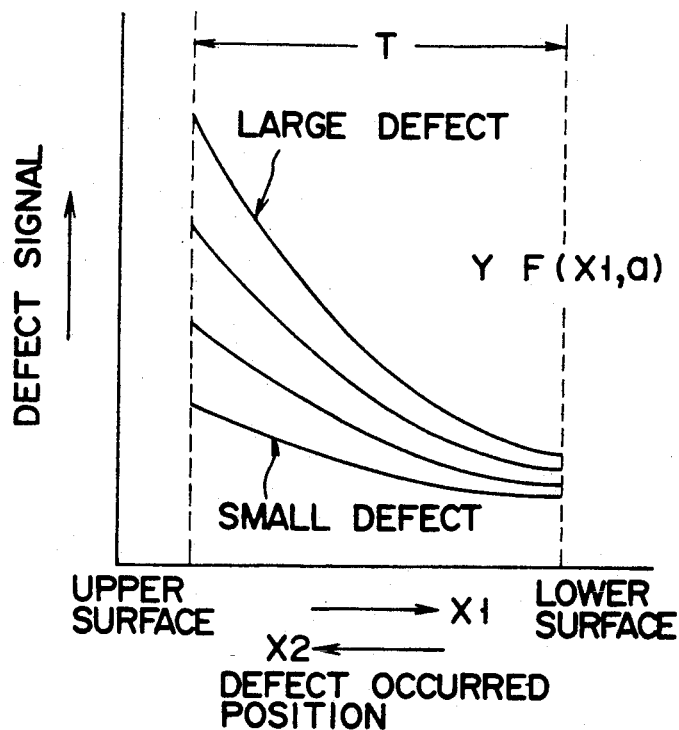
F I G. 18
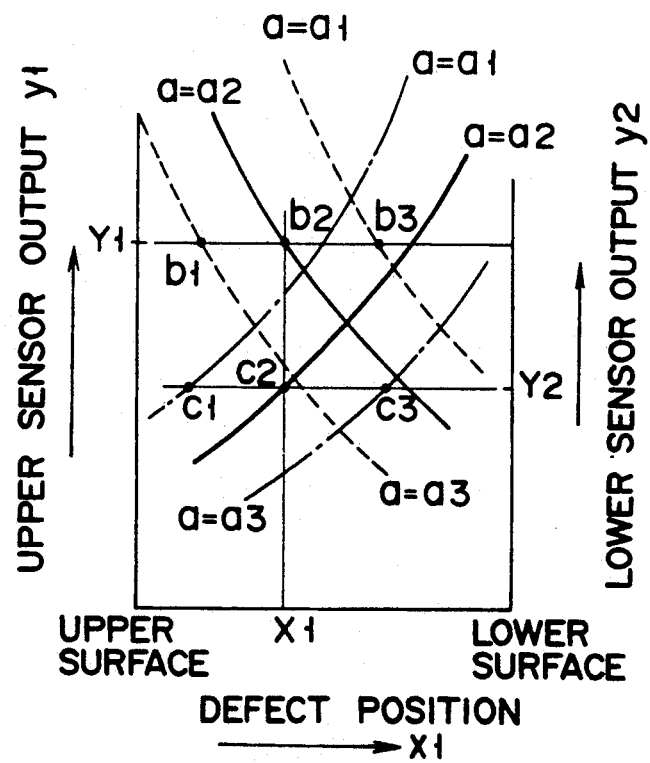
F I G. 19

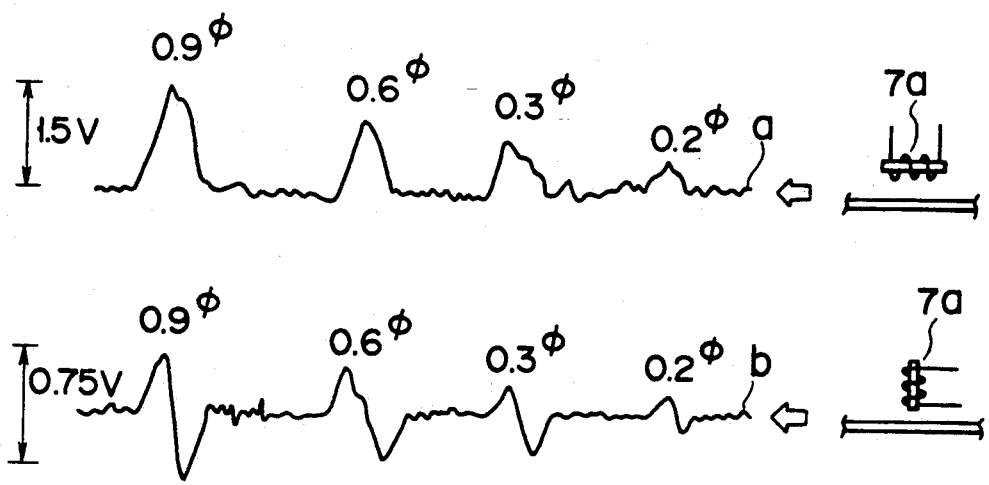
F I G. 33
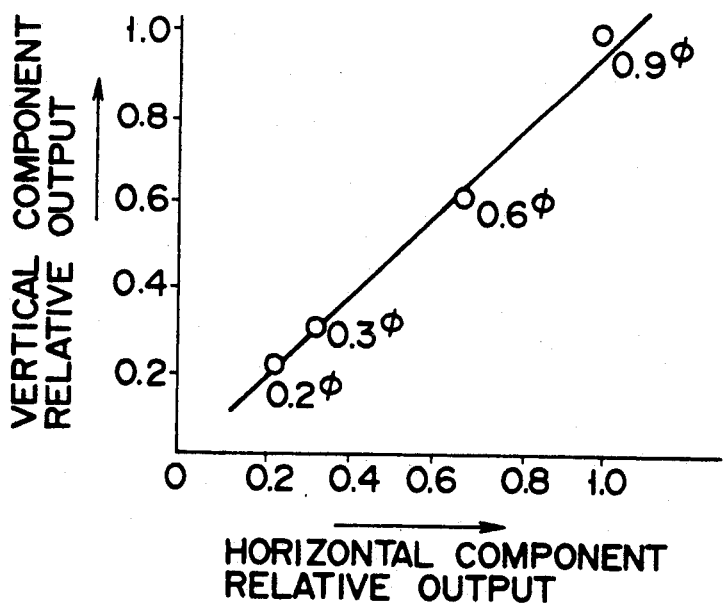
F I G. 34

MAGNETIC INSPECTION APPARATUS FOR THIN STEEL STRIP HAVING MAGNETIZER AND DETECTION COIL WITHIN A HOLLOW ROLLER ROTATED BY THE STEEL STRIP

TECHNICAL FIELD

The present invention relates to a magnetic inspection apparatus for a thin steel strip which detects a defect present in the interior or on the surface of a thin steel strip in a traveling state and, more particularly, to a magnetic inspection apparatus for a thin steel strip which urges a hollow roller, rotatably supported on a stationary shaft perpendicular to a travel path of the thin steel strip, against the steel strip. The magnetic inspection apparatus houses a magnetizer in the hollow roller, and detects by a magnetic sensor magnetic flux leakage occurring due to a defect.

BACKGROUND ART

A magnetic inspection apparatus detects a defect, e.g., a flaw or an inclusion, in the interior or on the surface of a thin steel strip by utilizing magnetism. A magnetic inspection apparatus for a thin steel strip which can not only examine a thin steel strip as an object to be examined in a still state but which also can continuously detect defects present in a thin steel strip traveling along, e.g., a manufacture, line of a factory and the like, has been disclosed in Published Unexamined Japanese Utility Model Application No. 63-107849.

FIGS. 31 and 32 are sectional views taken along different directions, respectively, of an above-described magnetic inspection apparatus for a thin steel strip which continuously detects defects of a traveling thin steel strip.

A hollow roller 1 is made of a non-magnetic material. One end of a stationary shaft 2 extends along the axis of the hollow roller 1. The other end of the stationary shaft 2 is fixed on the frame of a base (not shown). The stationary shaft 2 is supported on the inner circumferential surfaces of the two ends of the hollow roller 1 by a pair of rolling bearings 3a and 3b so that it is located along the axis of the hollow roller 1. Hence, the hollow roller 1 freely rotates about the stationary shaft 2 as the central axis of rotation.

Inside the hollow roller 1, a magnetization core 4c having a substantially U-shaped section is fixed on the stationary shaft 2 through a support member 5 such that the magnetization core 4c's magnetic poles 4a and 4b, which constitute a magnetic path, are close to the inner circumferential surface of the hollow roller 1. A magnetization coil 6 is wound around the magnetization core 4c. Hence, the magnetization core 4c with the magnetic poles 4a and 4b, and the magnetization coil 6 constitute a magnetizer 4. A plurality of magnetic sensors 7 are arranged between the magnetic poles 4a and 4b of the magnetization core 4c of the magnetizer 4 in the axial direction. Each magnetic sensor 7 is fixed on the stationary shaft 2.

A power cable 8 for supplying an excitation current to the magnetization coil 6 and a signal cable 9 for deriving the respective detection signals output from the respective magnetic sensors 7 extend to the outside through the interior of the stationary shaft 2. Hence, the positions of the magnetization core 4 and the respective magnetic sensors 7 are fixed, and the hollow roller 1 rotates at a small gap to the outer surfaces of the magnetizer 4 and the respective magnetic sensors 7.

When the outer circumferential surface of the hollow roller 1 of the magnetic inspection apparatus having such an arrangement is urged against one surface of a thin steel strip 10, traveling in the direction of an arrow A, at a predetermined pressure, the hollow roller rotates in the direction of an arrow B as the stationary shaft 2 is fixed on the frame of the base.

When an excitation current is supplied to the magnetization coil 6, a closed magnetic path is constituted by the magnetization core 4c and the traveling thin steel strip 10. Therefore, if a defect described above is present in the interior or on the surface of the thin steel strip 10, the magnetic path within the thin steel strip 10 is disturbed, and magnetic flux leakage occurs. The magnetic flux leakage is sensed by a magnetic sensor 7 at a corresponding position and is detected as a defect signal.

The signal level of the detected defect signal corresponds to the size of the defect in the interior or on the surface of the thin steel strip 10. Therefore, the presence and size of the defect of the thin steel strip 10 can be obtained in the form of the signal level of the defect signal.

However, the signal level of a defect signal is largely changed depending on the state of the magnetic path constituted by the thin steel strip 10 and the magnetizer 4 comprising the magnetization core 4c and the magnetization coil 6, a distance L between the magnetizer 4 and the thin steel strip 10, a distance l between the thin steel strip 10 and the respective magnetic sensors 7, which is called a lift-off distance, and so on.

In order to eliminate these drawbacks, the distance L between the thin steel strip 10 and the magnetizer 4 and the distance l between the thin steel strip 10 and the respective sensors 7 are constantly kept to be predetermined values by using the hollow roller 1 having a predetermined thickness t, as shown in FIGS. 31 and 32. If the hollow roller 1 is made of a magnetic material, formation of the magnetic path into the thin steel strip 10 is interfered. Therefore, the hollow roller 1 is made of a non-magnetic material.

Accordingly, the smaller the thickness t of the hollow steel strip 1, the smaller the distance L between the magnetic poles 4a and 4b of the magnetizer 4 and the thin steel strip 10, and the larger the magnetic field formed within the thin steel strip 10, thereby obtaining stable magnetic fluxes. For this reason, it is preferable that the thickness t of the hollow roller 1 be made small.

If the hollow roller 1 has a large thickness t, its moment of inertia becomes large. Then, when the travel speed of the thin steel strip 10 fluctuates, a sliding phenomenon may occur between the contact surfaces of the hollow roller 1 and the thin steel strip 10, which sliding phenomenon may damage the surface of the thin steel strip 10. Therefore, the l moment of inertia must be decreased by decreasing the thickness t of the hollow roller 1. When only the moment of inertia is to be decreased, the outer diameter of the hollow roller 1 may be set small. The outer diameter is restricted by the size of the magnetizer 4 or the magnetic sensors 7 housed in the hollow roller 1.

As described above, in order to continuously detect a defect in the traveling thin steel strip 10 with a high precision, as described above, the surface of the thin steel strip 10 must be in constant contact with the outer circumferential surface of the hollow roller 1. As a result, a downward force caused by the tension of the thin steel strip 10 and a downward force caused by the weight of the thin steel strip 10 itself are applied to the hollow roller 1. When a downward force is applied, the hollow roller 1 is deformed or damaged. Then, the distance L between the thin steel strip 10 and the magnetizer 4 and the distance l between the thin steel strip 10 and the respective magnetic sensors 7, described above, cannot be controlled to be the predetermined values. As a result, a defect detection precision may be degraded, or inspection may become impossible.

Hence, if the true circle state of the hollow roller 1 is to be kept over a long period of time, the thickness t of the hollow roller 1 should not be made smaller than a predetermined limit. For example, under the condition that the travel speed of the thin steel strip 10 is 100 m/min., the limit thickness t is about 2 mm.

The strength of the magnetic field generated by the magnetizer 4, housed in the hollow roller 1, comprising the magnetization core 4c and the magnetization coil 6 may be increased. However, if the size of the magnetization core 4c or the intensity of the current supplied to the magnetization coil 6 is increased over a predetermined limit, the entire apparatus must be made large, with the manufacturing costs being greatly increased.

DISCLOSURE OF INVENTION

It is the first object of the present invention to provide a magnetic inspection apparatus for a thin steel strip, in which the S/N ratio of a defect signal detected by a magnetic sensor can be increased without largely increasing the manufacturing costs, and a defect detection sensibility and a detection precision can be greatly increased.

In order to achieve the first object of the present invention, according to the present invention, the pole-to-pole distance of a magnetizer arranged in a hollow roller rotated as it contacts the surface of a traveling thin steel strip is set between twice or more and eight times or less of the distance between each magnetic pole and the thin steel strip.

As is known, in a magnetizer having a pair of separated magnetic poles, the magnetic fluxes output from one magnetic pole are input to the other magnetic pole through the space (magnetic gap) between magnetic poles. In this case, if a thin steel strip made of a magnetic material is present close to the magnetic gap, some of the magnetic fluxes output from one magnetic pole are input to the other magnetic pole through the thin steel strip without passing through the magnetic gap.

In this case, the ratio of the magnetic fluxes passing through the magnetic gap to those passing through the thin steel strip is largely influenced by the size (pole-to-pole distance W) of the magnetic gap and the distance L between each magnetic pole and the thin steel strip. More specifically, when the pole-to-pole distance W is constant, more magnetic fluxes are concentrated on a portion corresponding to one of the distances W and L of the magnetic circuit that has a smaller magnetic resistance. Therefore, when the distance between each magnetic pole and the thin steel strip becomes small, the density of the magnetic fluxes passing through the thin steel strip is increased accordingly; when the distance L becomes large, the density of the magnetic fluxes passing through the thin steel strip is decreased.

When the distance L is constant, the ratio of the magnetic fluxes passing through the thin steel strip to those passing through the magnetic gap is, increased as the pole-to-pole distance W is increased. However, when the pole-to-pole distance W is excessively increased, the strength of magnetic fluxes passing through the thin steel strip is decreased.

Hence, the pole-to-pole distance W has a predetermined optimum range. The optimum range is influenced by the distance L between each magnetic pole and the thin steel strip. More specifically, when the distance L is large, the optimum range is largely influenced by the pole-to-pole distance W; when small, it is largely influenced by the distance L.

The present inventors have obtained the relationship between the pole-to-pole distance W and the distance L through experiments and has confirmed that, if the pole-to-pole distance W falls within a range of twice to eight times the distance L ($2L \leq W \leq 8L$), magnetic fluxes passing through the thin steel strip have a sufficiently high density level.

Therefore, even if the distance L cannot be set small due to the limitations of the thickness of the hollow roller, as described above, the detection sensitivity of the magnetic sensor can be set maximum by setting the pole-to-pole distance W to satisfy the relationship described above, and a defect detection precision is improved.

According to the present invention, the position of the magnetic sensor in the travel direction of the thin steel strip is set at a position shifted from the central position of the magnetic poles to the travel direction side by a small distance determined by the residual magnetization characteristics of the thin steel strip.

Assume that a completely defectless thin steel strip is placed to oppose the magnetic poles of the magnetizer and the magnetization coil is excited by a DC power. In this state, when the position of the magnetic sensor is changed in the travel direction of the thin steel strip, the strength of the magnetic field detected by the magnetic sensors is maximum at one magnetic pole and is minimum to the other magnetic pole, exhibiting a vertical magnetic field distribution characteristic curve that crosses the 0 level line at the central position of the pole-to-pole distance W due to the floating magnetic flux. Therefore, if the magnetic sensor is set at the central position of the pole-to-pole distance W where the vertical magnetic field distribution characteristic curve crosses the 0 level line, the influences of the floating magnetic fluxes can be removed.

In the actual magnetic inspection apparatus, however, the thin steel strip travels in one direction at a constant speed. At this time, the thin steel strip is magnetized by the magnetizer, and the magnetic fluxes corresponding to the magnetization strength and the coercive force of the thin steel strip remain in the thin steel strip. As a result, a position where the vertical magnetic field distribution characteristic curve crosses the 0 level line is not always the central position of the pole-to-pole distance W but shifts in the travel direction side.

More specifically, when the thin steel strip travels, the central position of the pole-to-pole distance W does not correspond to the 0 level of the vertical magnetic field distribution characteristic curve. Rather, the 0 level position is shifted from the central position of the pole-to-pole distance W to the travel direction side. Hence, floating magnetic fluxes are present at the central position.

In short, according to the present invention, the magnetic sensor is moved to the shifted 0 level position. As a result, the magnetic sensor does not detect floating magnetic fluxes. Therefore, the detection sensibility of the magnetic sensor can be easily increased.

Further, according to the present invention, a pair of hollow rollers housing either a magnetizer or a magnetic sensor are arranged to sandwich a thin steel strip between them.

Hence, for example, the thickness of the hollow roller of a side to which the weight and tension force of the thin steel strip are directly applied is set large, and the thickness of the hollow roller of a side to which the weight and tension force of the thin steel strip are not directly applied is set small. When the magnetic sensor is housed in the thin hollow roller, the lift-off distance can be set short, and the defect detection sensibility can be improved.

Still further according to the present invention, the magnetic detection circuit for detecting magnetic flux leakage occurring due to a defect in the interior or on the surface of the thin steel strip comprises an over-saturation type magnetic sensor housed in the hollow roller and constituted by winding a detection coil around ferromagnetic core, excitation power supply means for exciting the magnetic sensor to an over-saturation range by supplying an AC power to the detection coil of the magnetic sensor through a stationary impedance, voltage detecting means for detecting positive and negative values of a voltage generated across two terminals of the detection coil, and arithmetic means for adding the positive and negative values that are detected by the voltage detecting means, and determining the sum as a measured value corresponding to the magnetic flux leakage.

Generally, an over-saturation type magnetic sensor obtained by applying a detection coil around a ferromagnetic core has a considerably excellent detection sensibility and a temperature characteristic when compared to those of a magnetic sensor which uses a magnetic diode, a magnetoresistive element, or a Hall element.

It is the second object of the present invention to provide a magnetic inspection apparatus for a thin steel strip, which can easily detect location and a size of a defect of a thin steel strip in the direction of the thickness. steel strip is arranged in each of the hollow rollers. A data processing unit calculates a defect occurring position in the direction of the thickness of the thin steel strip and a defect size from each magnetic flux leakage detected by each of the pair of magnetic sensors.

As the pair of hollow rollers contact the upper and lower surfaces of the steel strip, the distance between the upper surface of the steel strip and the corresponding magnetic sensor and that between the lower surface of the steel strip and the corresponding magnetic sensor are kept constant. A magnetic field is generated in the steel strip by the magnetizer. Therefore, if a defect is present, each magnetic sensor detects magnetic flux leakage corresponding to the defect. The magnetic flux leakage detected by each magnetic sensor can be expressed as a defect size and a distance to the defect, i.e., a function of the defect depth from the surface of the given magnetic sensor. As a result, the defect size and the defect position can be calculated by resolving the two functions as simultaneous equations.

BRIEF DESCRIPTION OF THE DRAWINGS

FIG. 3 is a sectional view of a test system for confirming the effect of the apparatus of the same embodiment;

FIG. 6 is a waveform chart of a defect signal obtained by the test system;

FIG. 18 is a graph of detect signal characteristics of the same;

FIG. 19 is a graph showing the steps of calculating a defect position and a defect size from the defect signal characteristics;

FIG. 33 is a view showing the relationship between the arrangement directions of the magnetic sensors and the detection output waveforms of the respective magnetic sensors, and FIG. 34 is a view showing the relationship between the vertical and horizontal magnetic fields detected by the respective magnetic sensors of FIG. 33.

BEST MODE FOR CARRYING OUT THE INVENTION

An embodiment of the present invention will be described with reference to the accompanying drawings.

Figure 1:
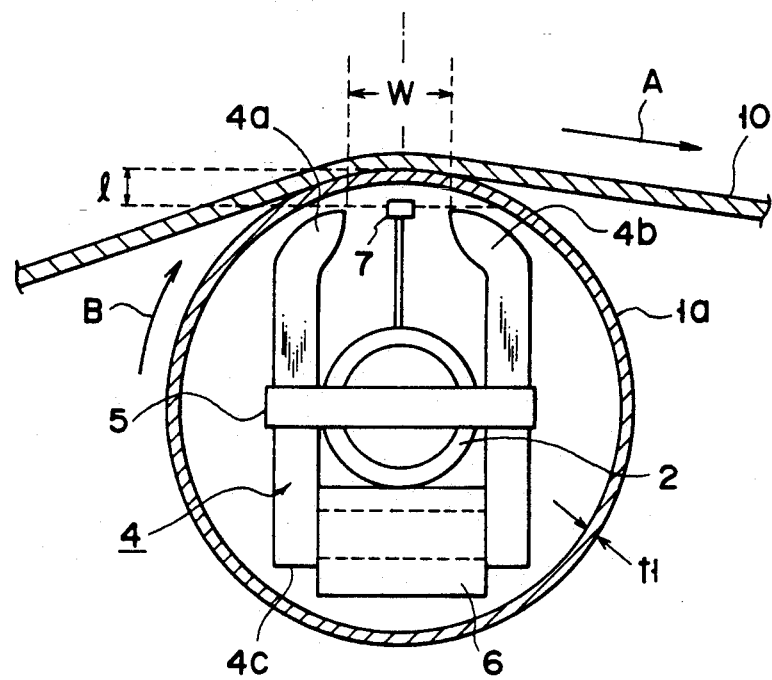
FIG. 1 is a sectional view of an embodiment of a magnetic inspection apparatus for a thin steel strip according to the present invention, along a plane parallel to the travel direction of the thin steel strip.
Figure 2:
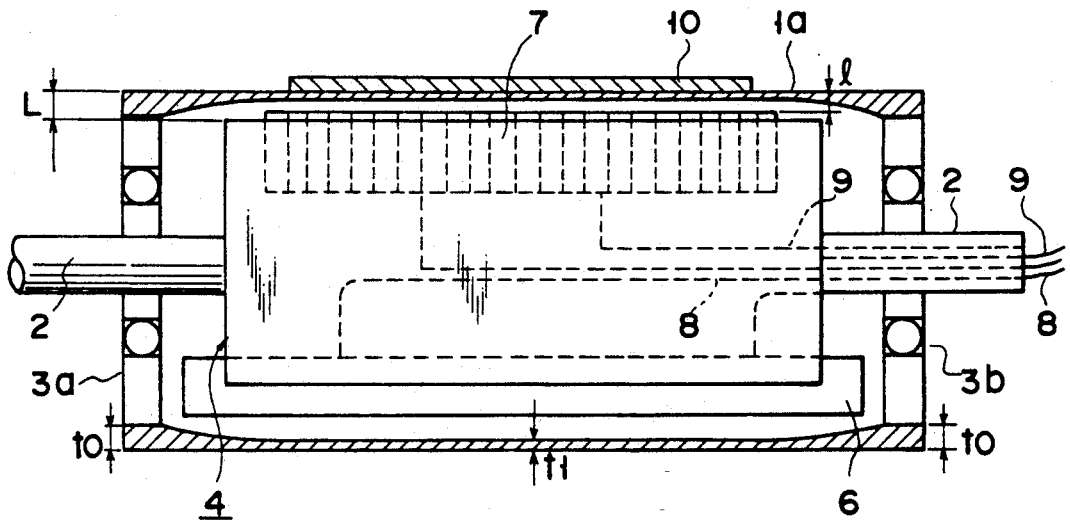
FIG. 2 is a sectional view of the apparatus of the same embodiment along a plane perpendicular to the travel direction of the thin steel strip.
Figure 31:
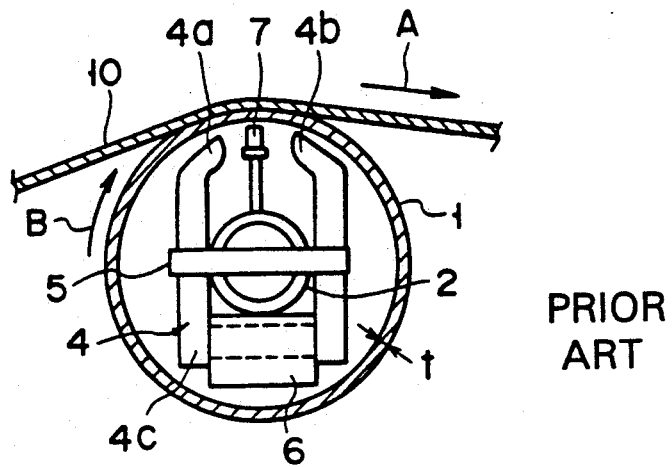
FIG. 31 is a sectional view of a general magnetic inspection apparatus for a thin steel strip along a plane parallel to the travel direction of the thin steel strip.
Figure 32:
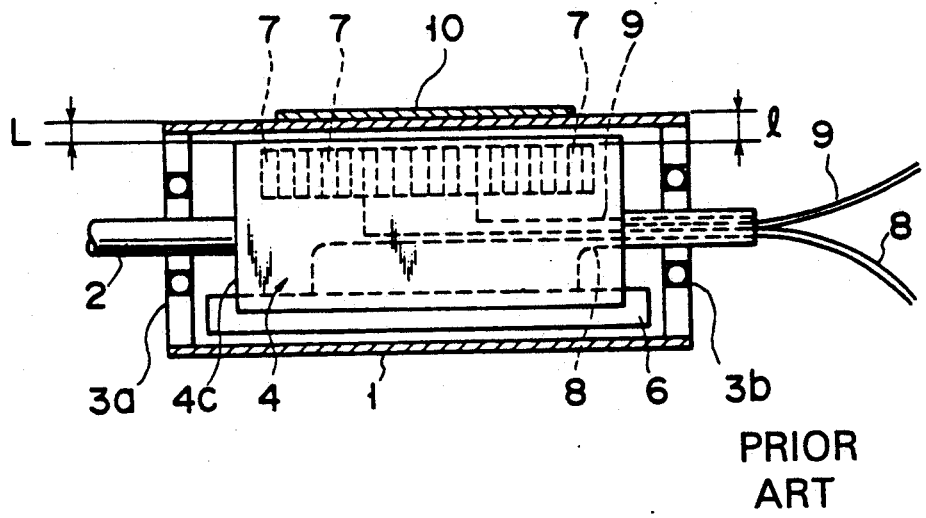
FIG. 32 is a sectional view of the conventional apparatus along a plane perpendicular to the travel direction of the thin steel strip.

FIGS. 1 and 2 are sectional views showing a schematic arrangement of an embodiment of a magnetic inspection apparatus. Note that the same portions as in the conventional apparatus shown in FIGS. 31 and 32 are denoted by the same reference numerals. Accordingly, a detailed description of overlapping portions is omitted.

One end of a stationary shaft 2 extends along the axis of a hollow roller 1a made of a non-magnetic material. The inner circumferential surfaces of the two ends of the hollow roller 1a are rotatably supported on the stationary shaft 2 by a pair of roll bearings 3a and 3b. Thus, the hollow roller 1a freely rotates about the stationary shaft 2 as the central axis of rotation.

Of the hollow roller 1a, a thickness $t_0$ of each end of it on which the roll bearing 3a or 3b is mounted is set large, and a thickness $t_1$ of its central portion to which a thin steel strip 10 contacts is set small, as shown in FIG. 2. In this embodiment, the thickness $t_0$ of each end is set to 6 to 10 mm, and the thickness $t_1$ of the central portion is set to be 1 to 4 mm.

In the hollow roller 1a, a magnetization core 4c having a substantially U-shaped section is fixed to the stationary shaft 2 through a support member 5 such that its magnetic poles 4a and 4b are close to the inner circumferential surface of the hollow roller 1a. The distal end of each of the magnetic poles 4a and 4b is curved to correspond to the radius of curvature of the inner circumferential surface of the hollow roller 1a. A magnetization coil 6 is wound around the magnetization core 4c. A plurality of magnetic sensors 7 are arranged between the magnetic poles 4a and 4b of the magnetization core 4c in the axial direction. Each magnetic sensor 7 is fixed to the stationary shaft 2. The magnetization core 4c and the magnetization coil 6 constitute a magnetizer 4 for generating a magnetic field in the thin steel strip 10 through the hollow roller 1a. Each magnetic sensor 7 uses an over-saturation type magnetic sensor described in Published Unexamined Japanese Patent Application No. 1-308982.

A power cable 8 for supplying an excitation current to the magnetization coil 6 and a signal cable 9 for deriving the detection signals output from the respective magnetic sensors 7 extend to the outside through the interior of the stationary shaft 2. Hence, the positions of the magnetization core 4c and the respective magnetic sensors 7 are fixed, and the hollow roller 1a rotates at a small gap to the outer surfaces of the magnetization core 4c and the respective magnetic sensors 7.

A pole-to-pole distance (magnetic gap size) W expressed as the distance between the magnetic poles 4a and 4b of the magnetizer 4 is set to be a value between twice or more and eight times or less than a distance L between the thin steel strip 10 and each of the magnetic poles 4a and 4b ($2L < W < 8L$).

The position of each magnetic sensor 7 in the travel direction of the thin steel strip 10 is set at substantially an intermediate position of the magnetic poles 4a and 4b. A lift-off distance l between each magnetic sensor 7 and the thin steel strip 10 is set at 3 mm in this embodiment.

When the outer circumferential surface of the hollow roller 1a of the magnetic inspection apparatus having such an arrangement is urged against one surface of the thin steel strip 10, which is traveling in, e.g., the direction of an arrow A, at a predetermined pressure, as the stationary shaft 2 is fixed to the frame of the base, the hollow roller 1a rotates in the direction of an arrow B.

When an excitation current is supplied to the magnetization coil 6 from an external magnetization power unit (not shown), a closed magnetic path is constituted by the magnetic poles 4a and 4b of the magnetization core 4c and the traveling thin steel strip 10. If a defect is present in the interior or on the surface of the thin steel strip 10, the magnetic path inside the thin steel strip 10 is disturbed, and magnetic flux leakage occurs. The magnetic flux leakage is detected by a magnetic sensor 7 at a given position as a defect signal.

The signal level of the detected defect signal corresponds to the size of the defect in the interior or on the surface of the thin steel strip 10. Hence, the presence and size of a defect in the interior or on the surface of the thin steel strip 10 can be determined from a change in a signal level of a defect signal.

An experimental result which explains why the pole-to-pole distance W of the magnetic poles 4a and 4b of the magnetizer 4 is set to be a value between twice or more and eight times or less than the distance L to the thin steel strip 10, as described above, will be described.

Referring to FIG. 3, a magnetization coil 33 is applied around a magnetization core 32, having separated magnetic poles 32a and 32b, to constitute a magnetizer 31. A thin steel strip 10 is arranged to be separated from the magnetizer 31 by a distance L. A magnetic sensor 7a is arranged on the other side of the thin steel strip 10 to be separated by a distance d. The position of the magnetic sensor 7a corresponds to the central position of a pole-to-pole distance W. Out of the magnetic fluxes of the magnitude field generated by the magnetizer 31, the magnetic sensor 7a indirectly detects the density of the magnetic fluxes passing through the thin steel strip 10. A plurality of magnetizers 31 having different pole-to-pole distances W are prepared. The distance L between the thin steel strip 10 and the magnetizer 31 can also be arbitrarily changed.

In such a test system, the magnetic sensor 7a was arranged such that its axis was perpendicular to the thin steel strip 10, and the vertical component of the magnetic flux leakage caused by each of four types of calibration flaws having outer diameters 0.2 mm to 0.9 mm formed in the thin steel strip 10 was measured. Similarly, the magnetic sensor 7a was arranged such that its axis was parallel to the thin steel strip 10, and the horizontal components of the magnetic flux leakages were measured under the same conditions. The measurement results are shown in FIG. 33. A signal waveform a is the horizontal component of the magnetic field, and a signal waveform b is the vertical component of the magnetic field.

Figure 9:
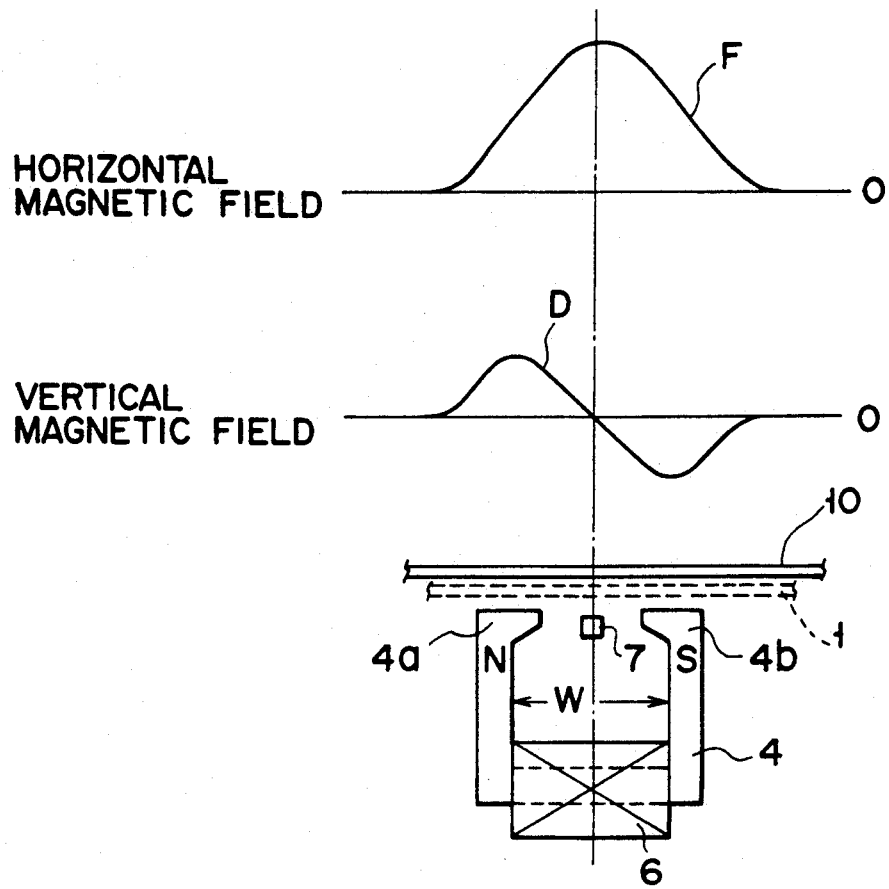
FIG. 9 shows the relationship among the respective magnetic poles, the horizontal magnetic field distribution, and the vertical magnetic field distribution.

FIG. 9 shows the positional relationship among the magnetic poles of the magnetizer, a horizontal magnetic field distribution characteristic F, and a vertical magnetic field distribution characteristic D. As shown in FIG. 9, the horizontal magnetic field distribution characteristic F has a substantially inverted U shape, and the vertical magnetic field distribution characteristic D has a waveform of substantially a sine curve.

In the embodiment of FIGS. 3, the distance L between the magnetizer 31 and the thin steel strip 10a is 3.5 mm, the pole-to-pole distance W is 20 mm, and the distance d between the magnetic sensor 7a and the thin steel strip 10a is 3 mm.

FIG. 34 shows the relationship between the relative outputs of the vertical and horizontal components of the magnetic field generated by each magnetic sensor 7a. As can be understood from the graph of FIG. 34, the horizontal and vertical components of the magnetic field have a positive correlation.

Based on this finding, the following embodiments exemplify a case in which a vertical component type magnetic sensor is used if not otherwise specified.

As shown in FIG. 33, the detection sensibility of a horizontal component detection type magnetic sensor is higher than that of a vertical component detection type magnetic sensor. When a horizontal component detection type magnetic sensor is used, however, a separate high-pass filter must be provided in order to extract a defect signal from magnetic noise of the object to be examined, e.g., a thin steel strip 10a, leading to a complicated circuit configuration.

Figure 4:
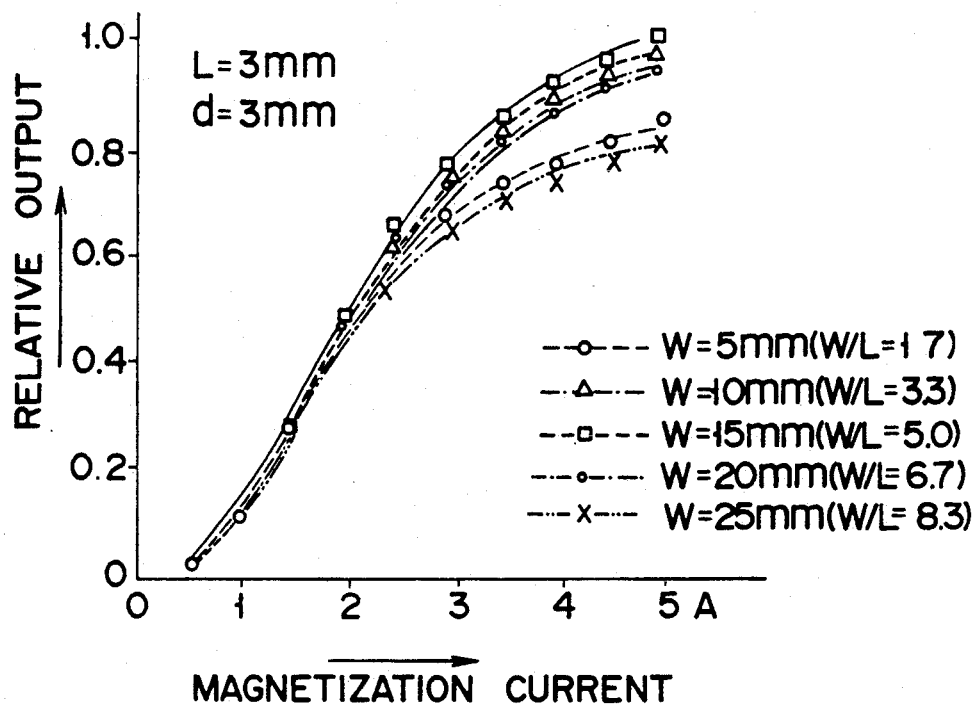
FIG. 4 is a graph of detection characteristics obtained by the test system.

An output voltage of the magnetic sensor 7a was measured while changing a pole-to-pole distance W of the magnetizer 31 from, e.g., 5 mm to 25 mm and fixing the distance L at a predetermined value, e.g., 3 mm. If no defect is present inside the thin steel strip 10a, the magnetic flux density inside it is measured by the magnetic sensor 7a as the magnetic flux leakage is proportional to the magnetic flux density inside the thin steel strip 10a. FIG. 4 shows the measurement result. In the experiment, the magnetization current supplied to the magnetization coil 33 is gradually increased from 0 A to rated 5 A.

It is understood that, when the magnetization current is increased, the density of the magnetic fluxes passing through the thin steel strip 10 is changed depending on the pole-to-pole distance W, as shown in FIG. 4. More specifically, in an area where the pole-to-pole distance W is excessively smaller than the distance L, such as where W=5 mm, the magnetic flux density is small. The magnetic flux density is also small in an area where the pole-to-pole distance W is excessively larger than the distance L, such as where W=25 mm. This tendency was observed within an area of $0.5 \mu m \leq L \leq 8.0$ m.m.

Figure 5:
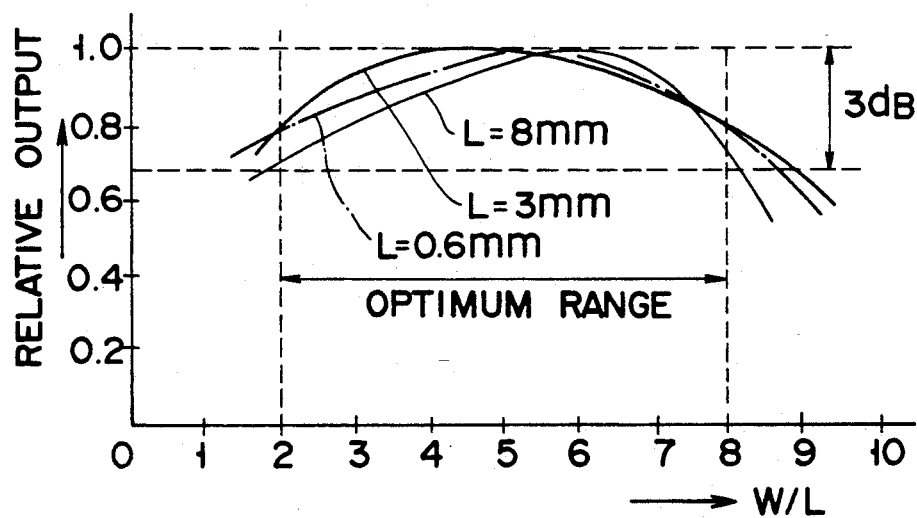
FIG. 5 is a graph of the detection characteristics of FIG. 4 but indicated by using a different parameter.

Characteristics shown in FIG. 5 are obtained by plotting a ratio (W/L) of the pole-to-pole distance W to the distance L along the axis of abscissa and a relative output of the magnetic sensor 7a along the axis of ordinate. More specifically, in FIG. 5, the pole-to-pole distance W is adjusted within an actually measured range of the distance L (0.5 mm$\leq$L$\leq$8.0 mm), and a maximum output for each distance L is indicated with respect to each pole-to-pole distance W normalized by the distance L.

Generally, the characteristics of a measuring device is evaluated with reference to [$-3$ dB]. In FIG. 5, a relative output of 70% or more is considered to be sufficiently used in practice. Hence, a range of W/L not less than 2 and not more than 8 is the optimum range.

FIG. 6 is a waveform chart of defect signals detected by the respective magnetic sensors 7 when the distance L between the magnetizer 4 and the thin steel strip 10 is changed from 1 mm to 5 mm in the actual apparatus shown in FIGS. 1 and 2 while the above condition (2L$\leq$W$\leq$8L) is satisfied. The signal waveforms of this chart are obtained by differentiating the vertical components of the magnetic fields. The experiment was conducted by using a thin steel strip 10 having three types of defect samples having predetermined pinhole outer diameters, i.e., 0.9 mm, 0.6 mm, and 0.3 mm.

When the distance L is increased, the signal level of an entire detected defect signal is decreased accordingly. However, the S/N ratio of the obtained detect signal is increased. Therefore, if the gain is increased by using an amplifier, even a small defect of, e.g., 0.3 mm, can be detected with a high precision.

As shown in FIG. 2, the thickness t of the hollow roller 1a is set large at two ends thereof on which the roll bearings 3a and 3b are mounted and small at the central portion thereof which contacts the thin steel strip 10. As described above, the thickness t of the hollow roller 1b is preferably small. However, if it is excessively small, the strength of the hollow roller 1a may be degraded. In order to compensate for the degradation in strength, the thickness $t_0$ of the hollow roller 1a at two ends thereon on which the roll bearings 3a and 3b are mounted is set larger than the thickness $t_1$ at the central portion thereof which the thin steel strip 10 contacts, thereby compensating for the degradation in strength caused by setting the overall thickness t of the hollow roller 1a to a certain degree.

As a result, the lift-off distance l expressed as the distance between the magnetic sensor 7 and the thin steel strip 10 can be set short, and thus the detection sensibility of the magnetic sensor 7 can be increased.

Figure 7:
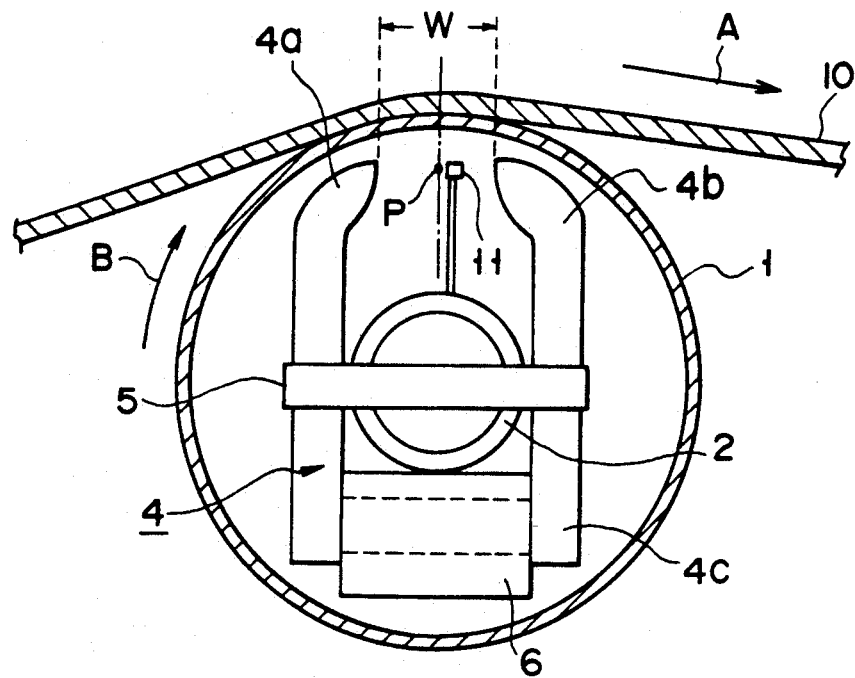
FIG. 7 is a sectional view of another embodiment of a magnetic inspection apparatus for a thin steel strip according to the present invention along a plane parallel to the travel direction of the thin steel strip.

FIG. 7 is a sectional view schematically showing the arrangement of another embodiment of the magnetic inspection apparatus for a thin steel strip according to the present invention. The same portions as those of the magnetic inspection apparatuses shown in FIGS. 31 and 1 are denoted by the same reference numerals. Thus, the detailed description of the overlapping portions is omitted.

In the magnetic inspection apparatus of this embodiment, the position of each magnetic sensor 11 mounted to a stationary shaft 2 in a hollow roller 1 in the travel direction of a thin steel strip 10 is set at a position shifted from a central position P of magnetic poles 4a and 4b by a small distance $\Delta X_0$ in the travel direction of the thin steel strip 10. In this embodiment, the small distance $\Delta X_0$ is set at 1 mm. A pole-to-pole distance W of a magnetizer 4 is set to be 56 mm, and a lift-off distance l between each magnetic sensor 11 and the thin steel strip 10 is set to be 3 mm.

Subsequently, the reason why the magnetic sensors 11 are shifted from the central position P of the magnetic poles 4a and 4b to the travel direction side of the thin steel strip 10 by the small distance $\Delta X_0$, as described above, and its effect will be described with reference to FIGS. 8 to 12.

FIG. 9 shows a vertical magnetic field distribution characteristic curve D of floating magnetic fluxes obtained when a completely defectless thin steel strip 10 is set still with respect to the magnetic poles 4a and 4b. As the thin steel strip 10 travels in one direction at a constant speed, magnetic fluxes corresponding to the coercive force of the thin steel strip 10 remain in the thin steel strip 10. As a result, the position where the vertical magnetic field distribution characteristic curve D crosses the 0 level does not necessarily correspond to the central position of the pole-to-pole distance W, but is shifted to the travel direction side.

Figure 10:
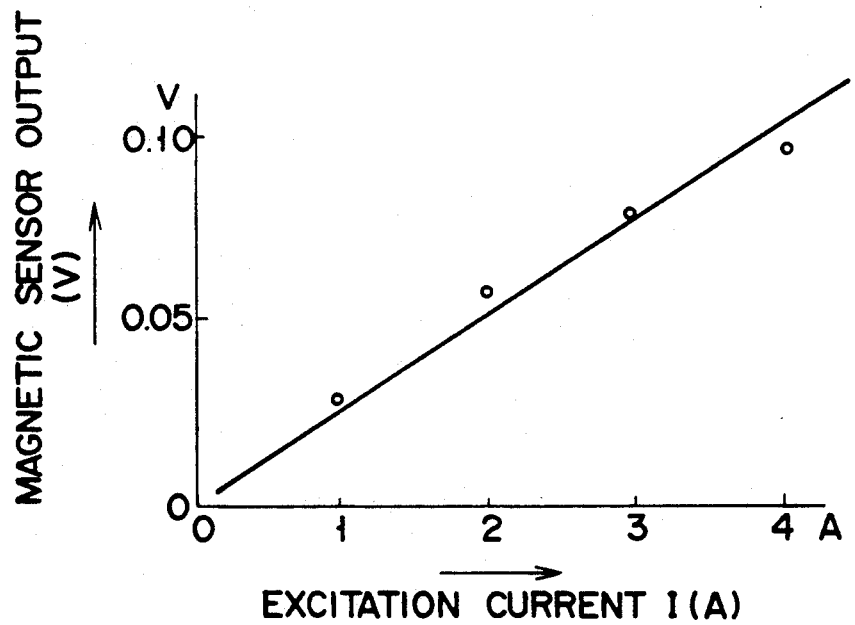
FIG. 10 is a graph of detection characteristics showing the relationship between an excitation current and a detection voltage of the magnetic sensor.

FIG. 10 shows actually measured values that represent the relationship between the excitation current and the detection voltage of the magnetic sensor 7 when a completely defectless thin steel strip 10 is caused to travel at a constant speed through a position opposing the magnetic poles 4a and 4b. It can be understood from FIG. 10 that when the excitation current is increased, the detected floating magnetic fluxes are increased.

Figure 8:
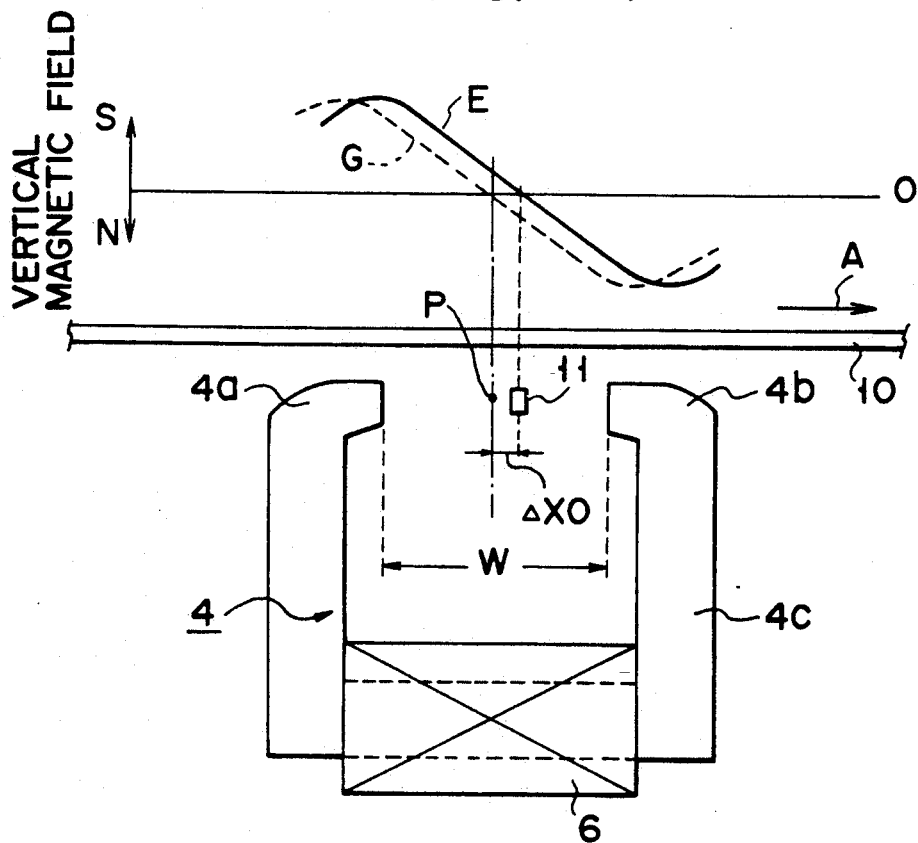
FIG. 8 is a schematic diagram of the main part of the embodiment of FIG. 7.

FIG. 8 is a schematic view of the main part of FIG. 7. A predetermined shift occurs between a vertical magnetic field distribution characteristic curve G, which is obtained when the completely defectless thin steel strip 10 is arranged to oppose the magnetic poles 4a and 4b, and a vertical magnetic field distribution characteristic curve E, which is obtained when the same thin steel strip 10 is caused to travel in the direction of an arrow A. This shift amount is substantially determined by the residual magnetization characteristics of the thin steel strip 10. Each magnetic sensor 11 is mounted at such a position in the travel direction where the vertical magnetic field distribution characteristic curve E becomes 0 level. In other words, this shift amount corresponds to the small distance $\Delta X_0$ described above. Hence, no floating magnetic flux is generated at a position where a magnetic sensor 11 is mounted.

If a floating magnetic flux component is not mixed in the detection voltage of a magnetic sensor 11, even if its detection sensibility is increased, the magnetic sensor 11 is not saturated. Thus, magnetic flux leakage caused by a defect, if small, can be detected at a high precision.

Figure 11:
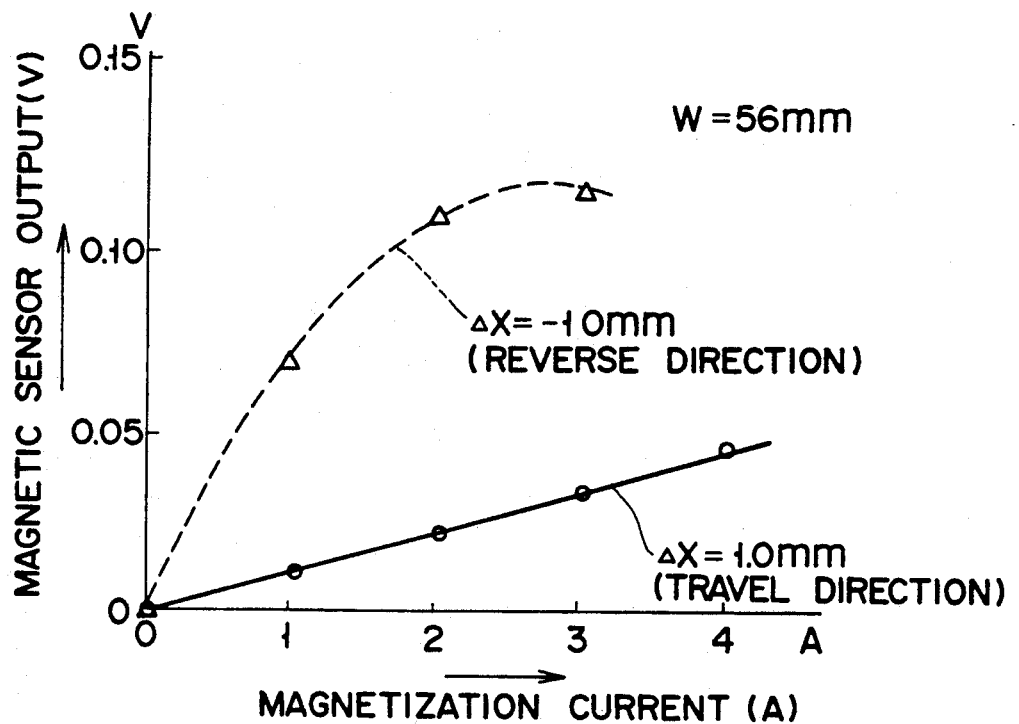
FIG. 11 is a graph of detection characteristics of the magnetic sensor when the magnetization current of the test system is changed.

FIG. 11 is a graph of actually measured values that indicates the relationship between a magnetization current applied to the magnetization coil 6 and the detection voltage of the magnetic sensors 11 when each magnetic sensor 11 is mounted at a position shifted from the central position P to travel and reverse directions of a completely defectless thin steel strip 10 by 1 mm, respectively, in the same manner as in this embodiment. The characteristic curve indicated as a solid line represents actually measured values obtained when the magnetic sensors 11 are shifted to the travel direction. The characteristic curve indicated as a broken line represents actually measured values obtained when the magnetic sensors 11 are shifted to the reverse direction. The pole-to-pole distance W is 56 mm.

As apparent from this experimental result, the vertical magnetic field generated by the floating magnetic fluxes detected by the magnetic sensors 11 when the magnetic sensors 11 are shifted in the travel direction is considerably smaller than that obtained when the magnetic sensors 11 are shifted in the reverse direction. Also, this vertical magnetic field is much smaller than the vertical magnetic field of the case of FIG. 10 which is detected when the magnetic sensors 7 are set at the central position P.

In other words, when the magnetic sensors 11 are shifted in the travel direction of the thin steel strip 10, the floating magnetic field detected by the magnetic sensors 11 is greatly reduced.

Figure 12:
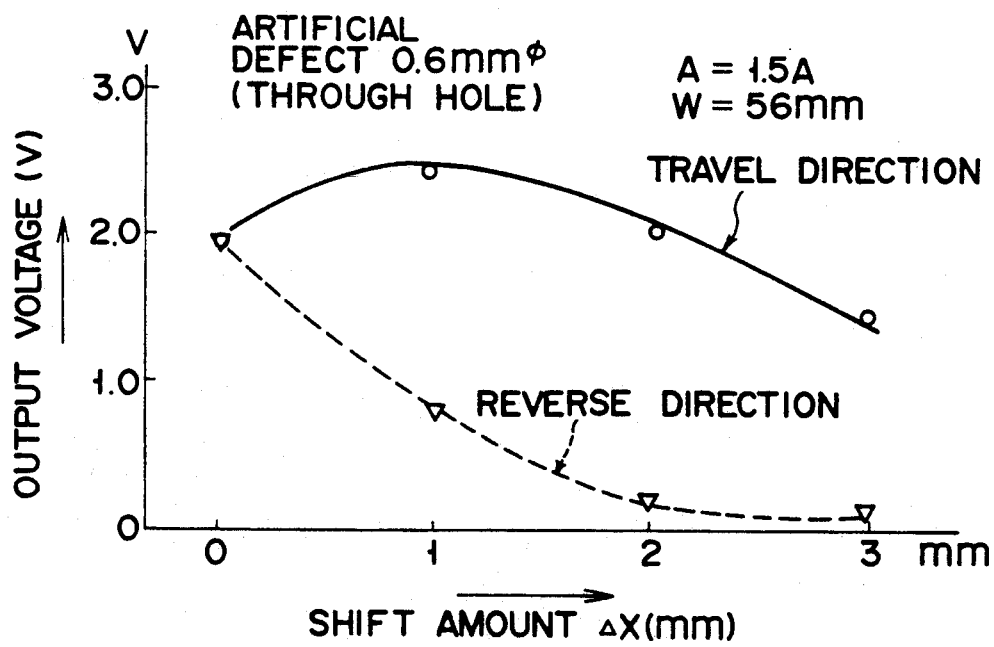
FIG. 12 is a graph of detection characteristics of the magnetic sensor when the position of the magnetic sensor in the test system is changed.

FIG. 12 shows the result of defect detection of a thin steel strip 10 in which a defect having a through hole having a diameter of 0.6 mm was artificially formed. This experiment shows a case indicated by a solid curve in which the positions of the magnetic sensors 11 were shifted in the travel direction, and a case indicated by a broken curve in which the positions of the magnetic sensors 11 were shifted in the reverse direction.

As indicated in FIG. 12, an optimum detection sensibility was obtained when the magnetic sensors 11 were shifted in the travel direction by a predetermined distance.

Even if the mount position of a magnetic sensor 11 in the travel direction (X direction) of the thin steel strip 10 is deviated a little, a fluctuation in detection sensibility against an artificial defect is small. Therefore, the magnetic sensors 11 can be easily mounted. For example, in the apparatus of this embodiment, an allowable range X of a mount position is $X = 1 \pm 0.5$ mm.

Figure 13:
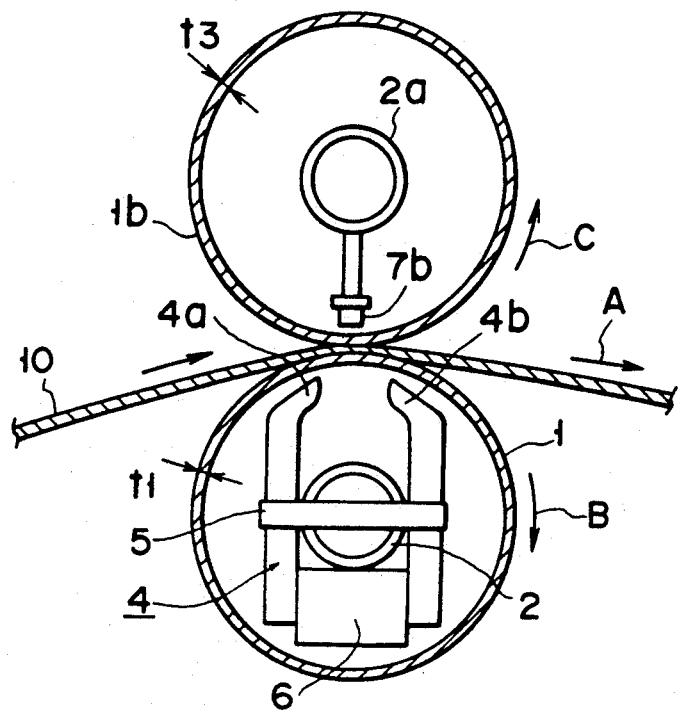
FIG. 13 is a sectional view of still another embodiment of a magnetic inspection apparatus for a thin steel strip according to the present invention along a plane parallel to the travel direction of the thin steel strip.
Figure 14:
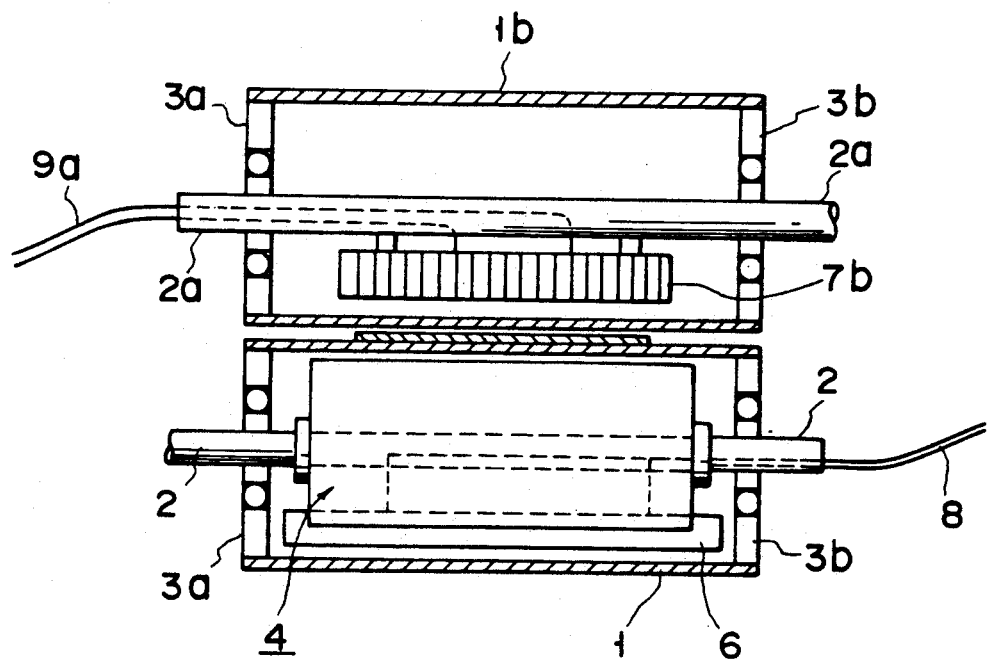
FIG. 14 is a sectional view of the same along a plane perpendicular to the travel direction of the thin steel strip.

FIGS. 13 and 14 are sectional views of still another embodiment of the magnetic inspection apparatus for a thin steel strip according to the present invention. Same portions as those of the magnetic inspection apparatuses shown in FIGS. 31, 32 and 1 are denoted by the same reference numerals. Hence, a detailed description of overlapping portions is omitted.

In the magnetic inspection apparatus of this embodiment, a pair of hollow rollers 1 and 1b are vertically arranged to sandwich a thin steel strip 10 between them. Each of the hollow rollers 1 and 1b is made of a non-magnetic material. The outer diameters of the hollow rollers 1 and 1b are set equal. However, a thickness $t_3$ of the upper hollow roller 1b is set smaller than a thickness $t_1$ of the lower hollow roller 1. One end of a hollow stationary shaft 2 extends along the axis of the hollow roller 1, and one end of a hollow stationary shaft 2a extends along the axis of the hollow roller 1b. The other end of the stationary shaft 2 of the lower hollow roller 1 is fixed on the frame of a base (not shown). The other end of the stationary shaft 2a of the upper hollow roller 1b is biased by a weak spring (not shown) toward the stationary shaft 2 of the lower hollow roller 1. The stationary shafts 2 and 2a are supported by the inner circumferential surfaces of the two ends of the hollow rollers 1 and 1b, respectively, through a pair of roll bearings 3a and 3b, such that they are located along the axes of the hollow rollers 1 and 1b, respectively. As a result, the hollow rollers 1 and 1b respectively rotate freely about the stationary shafts 2 and 2a as the central axes of rotation. When the thin steel strip 10 travels in the direction of an arrow A, the hollow rollers 1 and 1b are rotated in the directions of arrows B and C, respectively.

In the upper hollow roller 1b, a plurality of magnetic sensors 7b are fixed to the stationary shaft 2a through a support member such that they face downward. The distal end of each magnetic sensor 7b opposes the inner circumferential surface of the upper hollow roller 1b at a small gap. An output signal from each magnetic sensor 7b is supplied to the outside through a signal cable 9a extending through the interior of the stationary shaft 2a.

In the lower hollow roller 1, a magnetizer 4 is fixed to the stationary shaft 2 such that magnetic poles 4a and 4b of its magnetization core 4c face upward. The excitation current to a magnetization coil 6 is supplied through a power cable 8 extending through the interior of the stationary shaft 2.

A pole-to-pole distance W of the magnetizer 4 in the hollow roller 1 and a distance L between the magnetizer 4 and the thin steel strip 10 satisfy a predetermined relationship ($2L \leq W \leq 8L$) in the same manner as the embodiments described previously.

In the magnetic inspection apparatus of this type, since the weight or tension force of the thin steel strip 10 is not directly applied to the upper hollow roller 1b, the thickness $t_3$ of the upper hollow roller 1b can be set smaller than the thickness $t_1$ of the lower hollow roller 1. Thus, the detection sensibility of the magnetic sensors 7b can be further improved by setting the lift-off distance $l$ between the magnetic sensors 7b and the thin steel strip 10.

As the thin steel strip 10 is sandwiched between the upper and lower hollow rollers 1b and 1, vibration accompanying travel is suppressed. As a result, a fluctuation in a lift-off distance $l$ is decreased, leading to an increase in defect detection precision.

Figure 15:
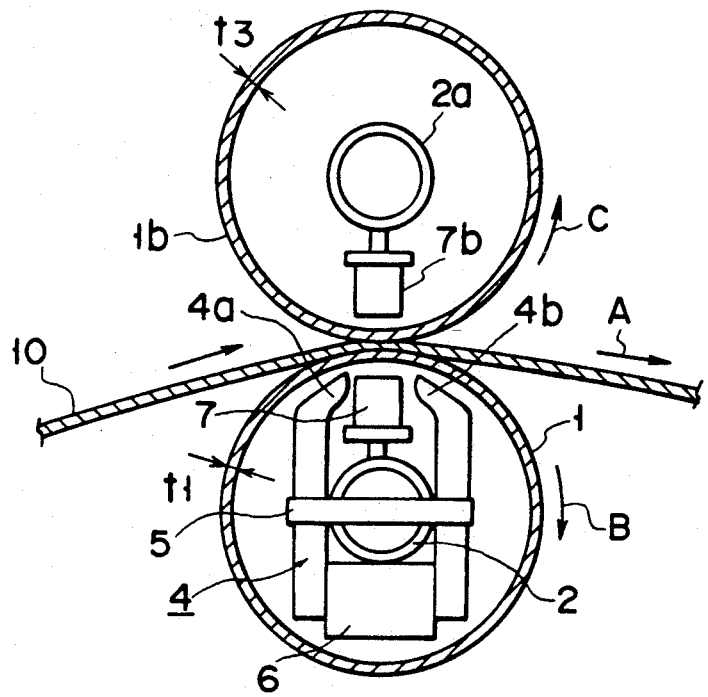
FIG. 15 is a sectional view of still another embodiment of the magnetic inspection apparatus for a thin steel strip according to the present invention along a plane parallel to the travel direction of the thin steel strip.
Figure 16:
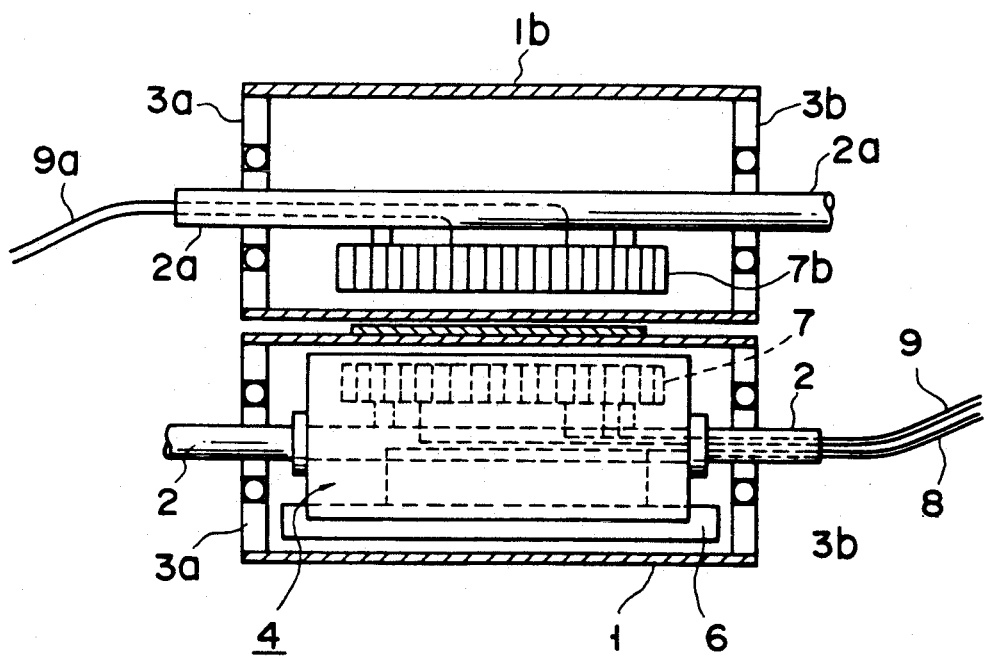
FIG. 16 is a sectional view of the embodiment of FIG. 15 along a plane perpendicular to the travel direction of the thin steel strip.

FIGS. 15 and 16 are sectional views schematically showing the arrangement of still another embodiment of the magnetic inspection apparatus for a thin steel strip according to the present invention. The same portions as those of the magnetic inspection apparatus shown in FIGS. 13 and 14 are denoted by the same reference numerals. Accordingly, a detailed description of overlapping portions is omitted.

In this embodiment, magnetic sensors 7 having the same arrangement as that of the magnetic sensors 7b housed in an upper hollow roller 1b are housed in a lower hollow roller 1.

Figure 17:
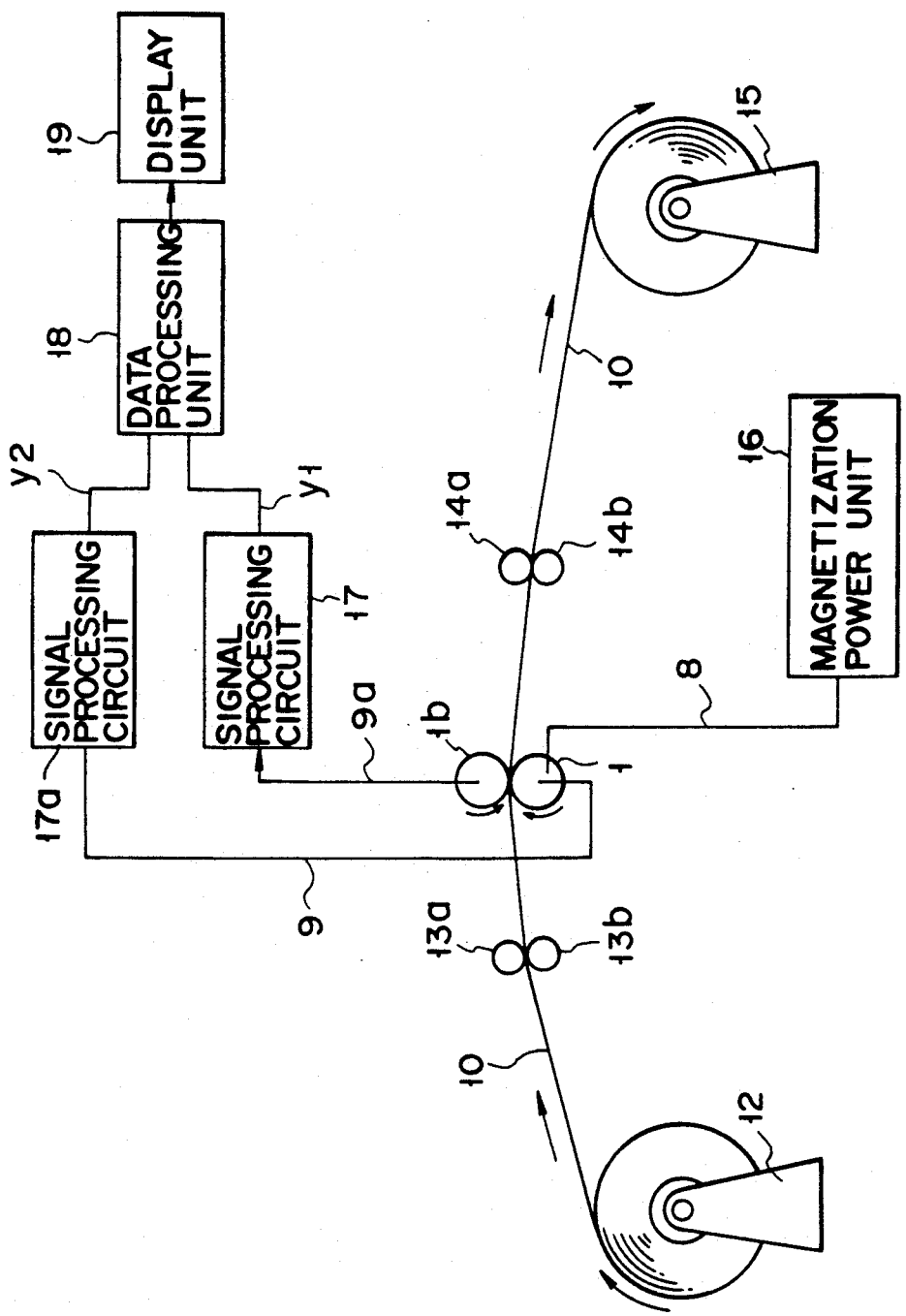
FIG. 17 is a schematic diagram showing the system of the entire apparatus of the embodiment of FIG. 15.

FIG. 17 shows the entire system of this magnetic inspection apparatus. The thin steel strip 10 fed from a supply reel 12 is guided to the pair of hollow rollers 1 and 1b through front press rollers 13a and 13b and is taken up by a take-up reel 15 through rear press rollers 14a and 14b at a constant speed. The lower hollow roller 1 is connected to a magnetization power unit 16 through the power cable 8. The hollow rollers 1 and 1b are connected to signal processing circuits 17a and 17 through the signal cables 9 and 9a, respectively. Defect signals $y_1$ and $y_2$ output from the signal processing circuits 17 and 17a are input to a data processing unit. The data processing unit 18 calculates a defect size a and a defect occurring position $X_1$ by using the input defect signals $y_1$ and $y_2$. The calculated defect size a and defect occurring position $X_1$ are displayed on a display unit 19 using, e.g., a CRT display.

The steps of calculating the defect occurring position $X_1$ in the thickness-wise direction of the thin steel strip 10 and the defect size a by using this magnetic inspection apparatus will be described.

The pair of hollow rollers 1b and 1 contact upper and lower surfaces, respectively, of the thin steel strip 10. Therefore, the distance between the magnetic sensors 7b and the upper surface of the thin steel strip 10 and the distance between the magnetic sensors 7 and the lower surface of the thin steel strip 10 are kept constant. Thus, a magnetic flux leakage value $Y_1$ detected by the magnetic sensors 7b if a defect is present can be expressed as a function of the defect size a and a distance to the defect, i.e., a depth $X_1$ from one surface of the thin steel strip 10 on the magnetic sensors 7b side and a magnetic flux leakage value $Y_2$ detected by the magnetic sensors 7 can be expressed as a function of the defect size a and a distance to the defect, i.e., a depth $X_2$ from the other surface of the thin steel strip 10 on the magnetic sensors 7 side:

$$Y_1 = F_1(X_1, a) \quad \ldots (1)$$

$$Y_2 = F_1(X_2, a) \quad \ldots (2)$$

These functions $F_1$ and $F_2$ can be approximated by, e.g., exponent attenuation curves, as shown in FIG. 18. In this embodiment, equations (1) and (2) are approximated as exponential functions as expressed in the following equations (3) and (4):

$$Y_1 = C_{11} \exp[C_{12}X_1 + a] \quad \ldots (3)$$

$$Y_2 = C_{11} \exp[C_{22}X_2 + a] \quad \ldots (4)$$

where $C_{11}$, $C_{12}$, $C_{21}$, and $C_{22}$ are constants that are experimentally obtained in advance.

As a thickness T of the steel strip is predetermined, $$T = X_1 + X_2 \quad \ldots (5)$$

The defect size a and the defect position $X_1$ can be obtained by resolving simultaneous equations (3), (4), and (5).

FIG. 19 schematically indicates the steps of calculating the defect position $X_1$ and the defect size a. When the defect size a is changed as $a = a_3$, $a = a_2$, and $a = a_1$, the characteristic curve of a defect signal $y_1$ is translated toward the right. When the defect size A is changed as $a = a_3$, $a = a_2$, and $a = a_1$, the characteristic curve of a defect signal $y_2$ is translated to the left.

Hence, points on the characteristic curves corresponding to the measured signal value $Y_1$ are $b_1$, $b_2$, and $b_3$. Similarly, points on the characteristic curves corresponding to the measured signal value $Y_2$ are $c_1$, $c_2$, and $c_3$. Accordingly, points where the defect sizes a are equal and simultaneously satisfying the signal values $Y_1$ and $Y_2$ are the points $b_2$ and $c_2$. As a result, the position $X_1$ corresponding to these points $b_2$ and $c_2$ is the defect occurred position, and the given detect size $a_2$ is the defect size a of the corresponding defect.

With the magnetic inspection apparatus for the thin steel strip having the above arrangement, the position $X_1$ and the size a of a defect present in the interior or on the surface of the thin steel strip 10 can be accurately obtained by simple calculation equations from the defect signals $y_1$ and $y_2$ of the thin steel strip 10 respectively detected by the magnetic sensors 7b and 7 arranged in the pair of hollow rollers 1b and 1 that oppose each other to sandwich the thin steel strip 10 as the inspection target.

Since the defect occurred position $X_1$ and the defect size A can be accurately obtained, the type of the defect can substantially be accurately obtained. The types of defects that can be obtained with this magnetic inspection apparatus include a visible gauge, an invisible gauge, a weld, a blow hole, a hole, an edge tongue flaw, an ear crack flaw, a trimmer flaw, and the like.

Since the defect occurring position, the detect size, the defect type, and so on can be accurately obtained, in this manner, when this magnetic inspection apparatus is incorporated in the testing line of a factory, the test data obtained by it can be used as significant information in improving the product quality.

The magnetic sensors 7b and 7 are housed in the hollow rollers 1b and 1, respectively. The hollow rollers 1b and 1 are constantly urged against the upper and lower surfaces, respectively, of the thin steel strip 10 by a predetermined biasing force. Therefore, the distance between the magnetic sensors 7b and the upper surface of the thin steel strip 10 and the distance between the magnetic sensors 7 and the lower surface of the thin steel strip 10 can be constantly kept to be constant values. Hence, even if the thin steel strip 10 is vertically vibrated during traveling, the distances to it are kept to be the constant values, and thus the defect measuring precision is further improved.

Figures 20, 21:
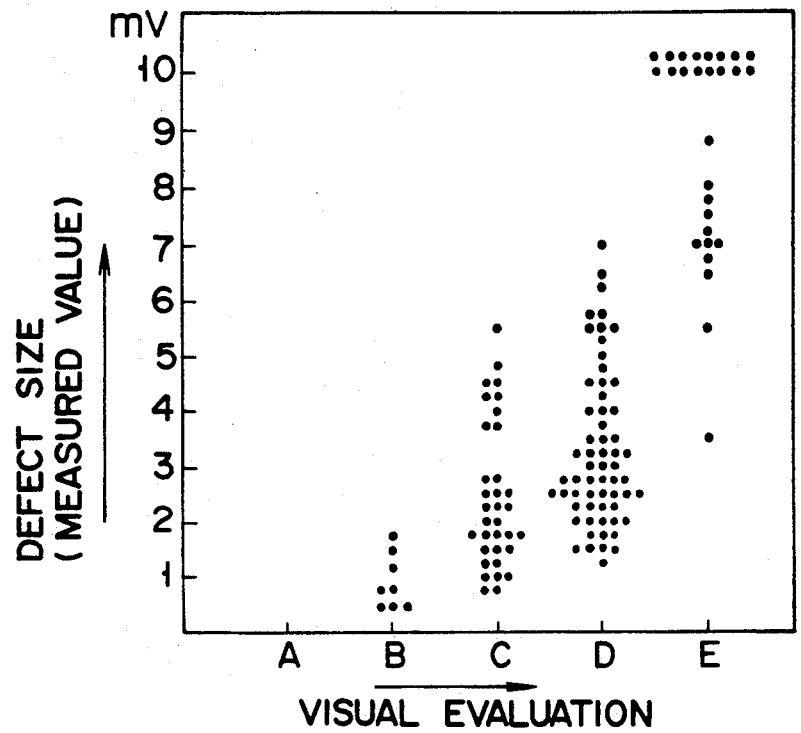
FIG. 20 is a graph showing the relationship between a measured value and a human visual evaluation.
FIG. 21 is a table showing the relationship among the respective measured values, the defect positions, and the defect sizes of a still another embodiment of a magnetic inspection apparatus.

FIG. 20 shows a correspondence between defect sizes of actually measured defects and their evaluation results obtained by actually revealing the measured defects by cutting or the like and visually evaluating the defect sizes in terms of 5 levels of A to E by an observer. It is understood that the measured defect sizes highly correspond to their visual evaluations.

The present invention is not limited to the embodiments described above. In the data processing unit 18 of the embodiment, in order to calculate the defect occurring position $X_1$ and the defect size a from the signal values $Y_1$ and $Y_2$, the defect signals $y_1$ and $y_2$ are approximated by exponential functions indicated in equations (3) and (4). However, if approximation to a simple function is impossible, a large number of calibration flaw samples having known defect positions and defect sizes are used for measurement. The relationship among the signal values $Y_1$ and $Y_2$ of the magnetic sensors 7b and 7, respectively, the defect position $X_1$, and the defect size a can be stored in the form of a table, as shown in FIG. 21. The table of FIG. 21 may be retrieved by using the measured values $Y_1$ and $Y_2$ obtained by actually measuring the thin steel strip 10, and a pair of values $Y_1$ and $Y_2$ closest to the actually measured values $Y_1$ and $Y_2$ may be found. Then, a defect position and a defect size corresponding to the pair of the sample values $Y_1$ and $Y_2$ may be read out and determined as the measurement result.

A magnetic detection circuit which is used for detecting, by using an over-saturation type magnetic sensor, magnetic flux leakage caused in the interior or on the surface of the thin steel strip 10 magnetized by the magnetizer 4 housed in the hollow roller will be described.

Figure 22:
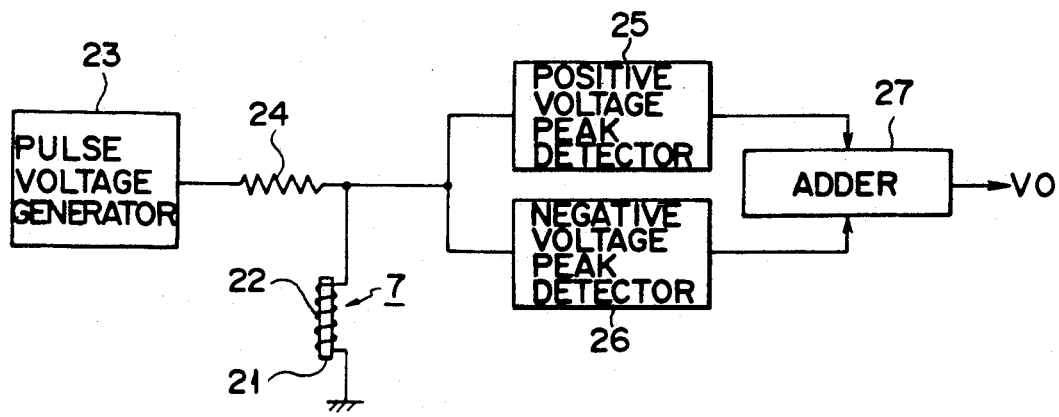
FIG. 22 is a block diagram showing a magnetic detection circuit of still another embodiment of a magnetic inspection apparatus for a thin steel strip according to the present invention.

FIG. 22 is a block diagram showing the schematical arrangement of the magnetic detection circuit.

Figure 23:
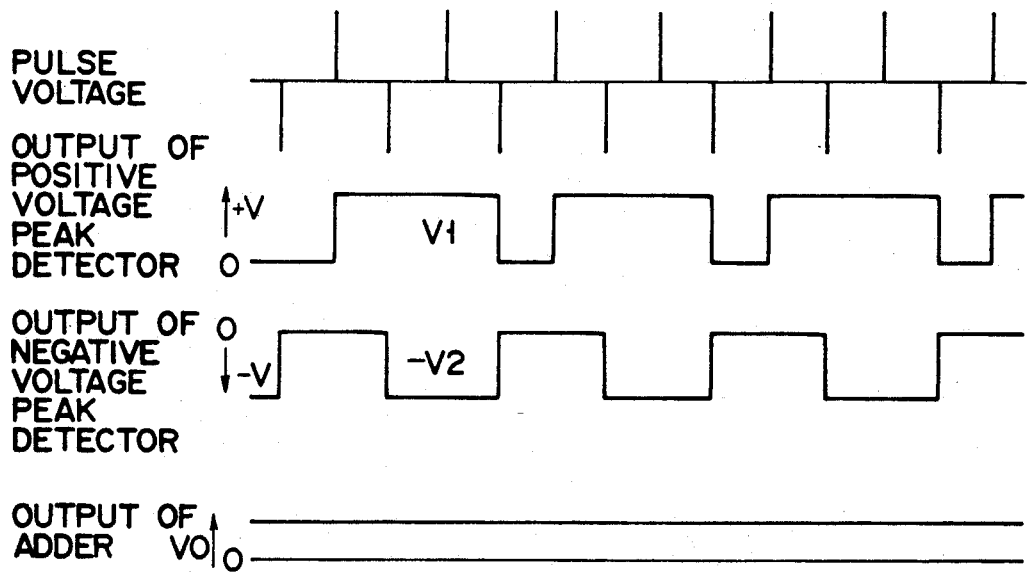
FIG. 23 is a timing chart showing the operation of the magnetic detection circuit.

An over-saturation type magnetic sensor 7 comprises a rod-like ferromagnetic core 21 and a detection coil 22 applied around the ferromagnetic core 21. A pulse voltage generator 23 outputs positive and negative pulse voltages at an equal interval, as shown in FIG. 23. The output terminal of the pulse voltage generator 23 is connected to one terminal of the detection coil 22 of the over-saturation type magnetic sensor 7 through a resistor 24 as a stationary impedance. The other terminal of the detection coil 22 is grounded. A pulse voltage output from the pulse voltage generator 23 is applied to the detection coil 22. As a result, the ferromagnetic core 21 is magnetized to an over-saturation range.

The one end of the detection coil 22 is connected to the input terminals of a positive voltage peak detector 25 and a negative voltage peak detector 26. The peak detectors 25 and 26 detect positive and negative peak values $V_1$ and $-V_2$, respectively, of an input signal. The peak values $V_1$ and $-V_2$ obtained by the peak detectors 25 and 26 are input to an adder 27. The adder 27 adds the peak value $V_1$ with the peak value $-V_2$ and outputs an output voltage $V_0$.

The operation principle will be described with reference to FIGS. 24 to 28.

Figure 24:
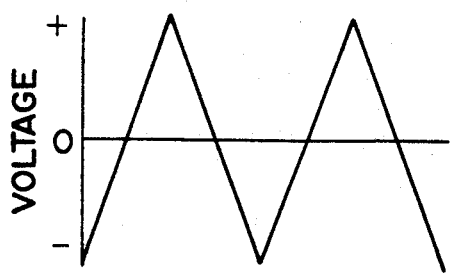
FIG. 24 is a waveform chart of a voltage applied to the detection coil of the magnetic detection circuit.

An AC power having an AC voltage waveform as shown in FIG. 24 is applied to the detection coil 22 of the magnetic sensor 7 through the resistor 24. Then, a voltage $e_0$ generated across the two terminals of the detection coil 22 is determined in accordance with a resistance R of the resistor 24 and an impedance Zs of the detection coil 22. Namely, it is expressed as:

$$e_0 = e \cdot Z_s/(R+Z_s) \qquad \ldots (6)$$

where e is a voltage to be applied.

As the detection coil 22 is applied around the ferromagnetic core 21, the impedance Zs changes in proportion to the magnetic permeability of the ferromagnetic core 21.

Figure 27:
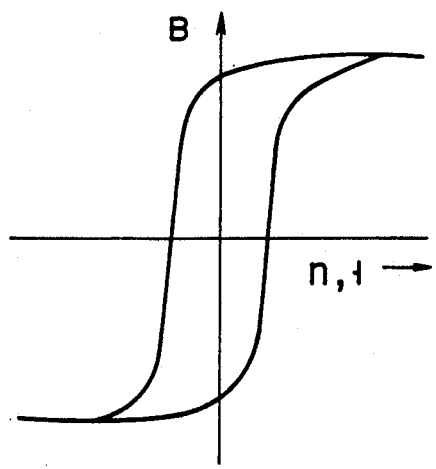
FIG. 27 is a graph of magnetization characteristics of a ferromagnetic core.

Assume that an AC current is supplied to the detection coil 22 without applying an external magnetic field to the magnetic sensor 7. As shown in FIG. 27, the magnetic permeability of the ferromagnetic core 21 changes in accordance with the hysteresis characteristic of the core 21. Note that reference symbol n denotes the number of coil turns; and i, a coil current.

Figure 25:
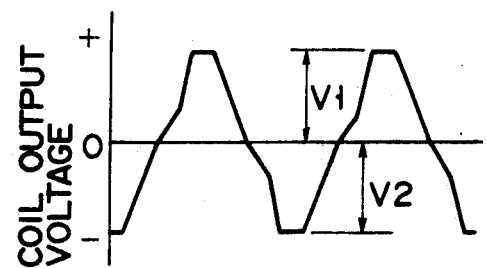
FIG. 25 is a waveform chart of a voltage output from a coil of the magnetic detection circuit.

As a result, an output voltage generated across the two terminals of the detection coil 22 has a waveform as shown in FIG. 25. When the external magnetic field is not applied, the positive and negative waveforms are symmetrical to each other, and the positive voltage $V_1$ is equal to the negative voltage $V_2$.

Figure 26:
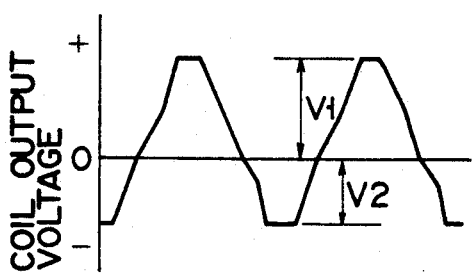
FIG. 26 is also a waveform chart of a voltage output from the coil of the magnetic detection circuit.

In this state, when an external magnetic field is applied, the magnetic fluxes intersecting the ferromagnetic core 21 become the composite magnetic flux of the magnetic field generated by the detection coil 22 and the external magnetic field. Thus, the waveform generated across the two terminals of the detection coil 22 is $V_1 > V_2$, as shown in FIG. 26.

Accordingly, the external magnetic field can be indirectly measured by comparing the positive and negative voltages $V_1$ and $V_2$ of the output voltage generated across the two terminals of the detection coil 22 and obtaining their difference. In the magnetic inspection apparatus, an external magnetic field corresponds to the strength of the magnetic flux leakage caused by a defect.

Figure 28:
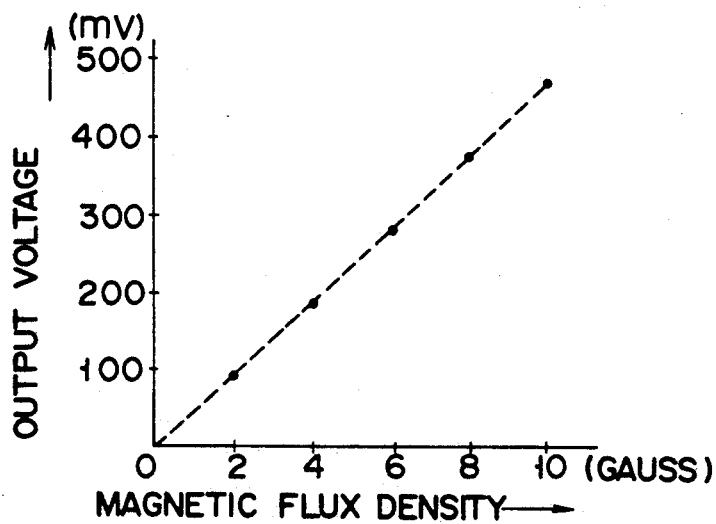
FIG. 28 is a graph of an output voltage with respect to the magnetic flux density of the magnetic detection circuit.

When the over-saturation type magnetic sensor 7 having such an arrangement is used, an output voltage $V_0$ of 0 to 500 mV can be obtained for a weak magnetic flux density of 0 to 10 gauss, as shown in FIG. 28.

In the magnetic detection circuit of the arrangement shown in FIG. 22, the AC power applied to the magnetic sensor 7 has positive and negative pulse voltage waveforms as shown in FIG. 23.

Since the pulse voltage is supplied to the detection coil 22 of the magnetic sensor 7 in this manner, the power consumption is decreased compared to a case in which the ordinary AC power shown in FIG. 24 is supplied, leading to energy saving. For example, if the ratio of the pulse width to the pulse period of the pulse voltage is set to 10 to 100, the average power supplied to the magnetic sensor 7 can be suppressed to about 1/10 to 1/100. As a result, a battery can be sufficiently used as the power source of the magnetic inspection apparatus.

As the peak values of the voltage generated across the two terminals of the detection coil 22 are detected, the relative detection sensibility of the weak magnetic flux is not substantially changed even if the ratio of the pulse width to the pulse period described above is changed over a wide range of 2 to 100.

As the power consumption is low, even if a large number of magnetic sensors 7 are arranged in the magnetic inspection apparatus in the widthwise direction of the thin steel strip 10, the power consumption is not greatly increased.

Figure 29:
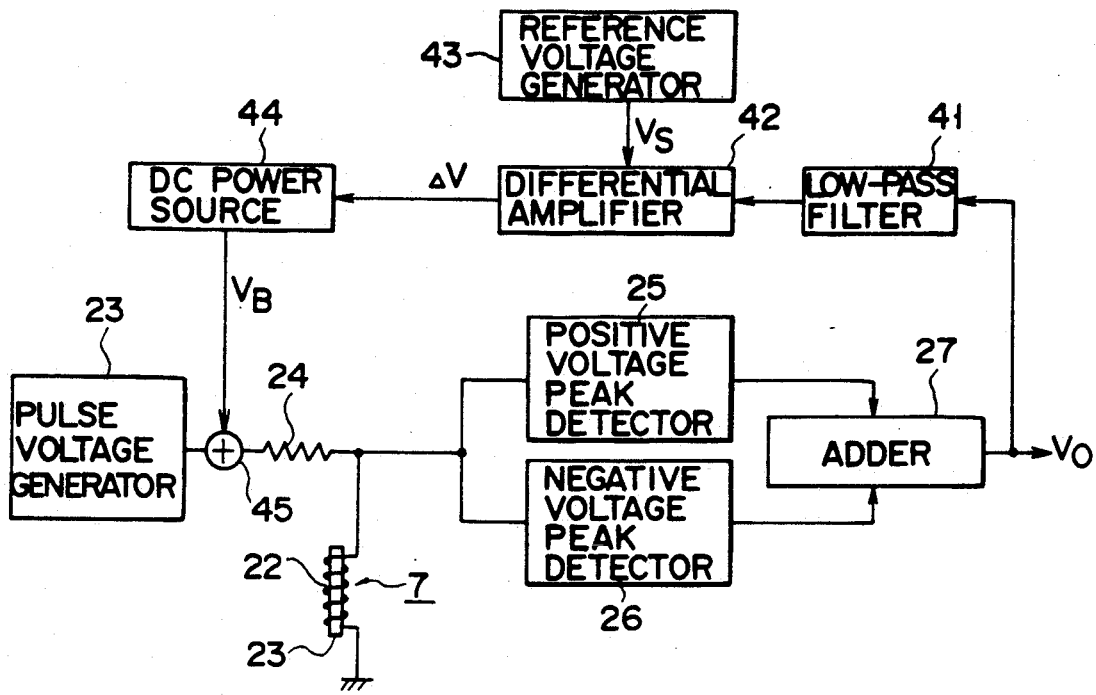
FIG. 29 is a block diagram showing a magnetic detection circuit of a still another embodiment of the present invention.

FIG. 29 is a block diagram schematically showing another arrangement of a magnetic detection circuit.

In the magnetic detection circuit of this arrangement, a bias circuit for applying a DC bias voltage to the pulse voltage to be applied to the magnetic sensor 7 is added to the circuit of FIG. 22.

An output voltage $V_0$ from an adder 27 is converted into a DC voltage by a low-pass filter 41 and is input to a differential amplifier 42. The differential amplifier 42 outputs a differential voltage $\Delta V$ between the input voltage $V_0$ and a reference voltage $V_S$ output by a reference voltage generator 43. The differential voltage $\Delta V$ output from the differential amplifier 42 is input to a DC power source 44. The DC power source 44 applies, through an adder 45, a DC bias voltage $V_B$ proportional to the differential voltage $\Delta V$ to the pulse voltage to be applied to the magnetic sensor 7.

The effect obtained by applying the DC bias voltage $V_B$ to the pulse voltage will be described.

Figure 30:
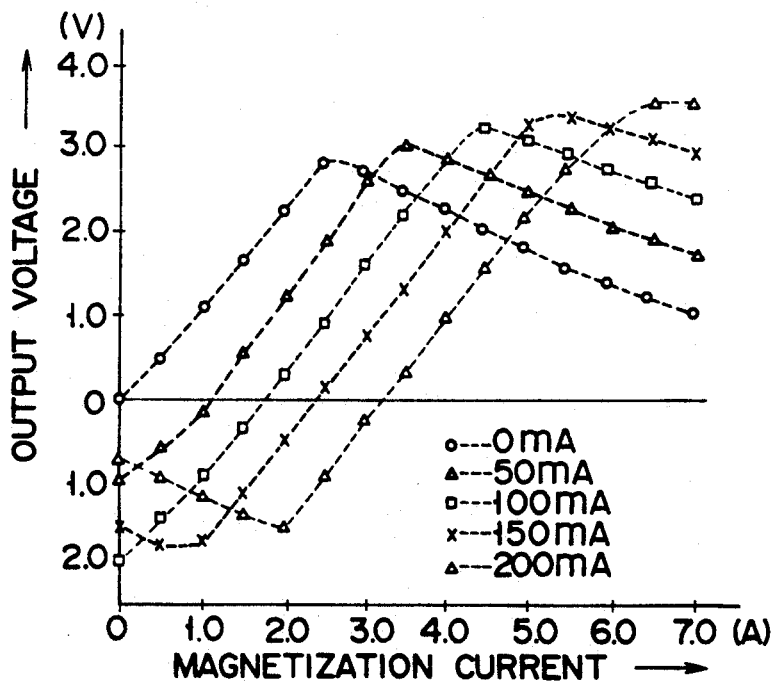
FIG. 30 is a graph of an output voltage with respect to the magnetization current of the magnetic detection circuit of the embodiment of FIG. 29.

FIG. 30 is a graph showing the result obtained by measuring the relationship between the magnetization current and the output voltage of the detection coil 22 while changing the DC bias current from the DC power source 44 to 0 mA, 50 mA, 100 mA, 160 mA, and 200 mA.

For example, when a DC vias current of 0 mA is supplied, the linear characteristic range of the output voltage with respect to the magnetization current is 0 to 2.5 A. When a DC bias current of 100 mA is supplied to the detection coil 22, the linear characteristic range is widened to 0 to 4.5 A. In this manner, the measurement span can be increased by changing the DC bias current, thus improving the defect detection precision.

When the DC bias current is further increased over 100 mA, although the measurement span is not changed, the measurement range of a magnetic flux leakage shifts. Inversely, the DC bias current may be controlled such that, when a thin steel strip 10 completely free from a defect is magnetically examined, the output voltage $V_0$ is constantly 0 V.

In the magnetic detection circuit shown in FIG. 29, the bias voltage $V_B$ proportional to the differential voltage $\Delta V$ between the output voltage $V_0$ and the reference voltage $V_S$ is applied to the pulse voltage. Therefore, if no defect is present, the output voltage $V_0$ is automatically controlled to 0 V. The frequency response of the control loop is low whereas the defect of a traveling thin steel strip 10 is expressed as a high frequency component. Therefore, the defect is reliably detected.

In this manner, the operation point is automatically corrected to the central portion of the measurement range of the magnetic detection circuit. Even if the measurement conditions change, a good measurement range can be constantly obtained, and the defect detection performance can be further improved.

We claim:

1. A magnetic inspection apparatus for a thin steel strip, comprising:
    a hollow roller, rotatably supported by a stationary shaft perpendicular to a travel path of a thin steel strip and rotated by being contacted by a surface of the thin steel strip traveling along the travel path;
    a magnetizer, arranged in said hollow roller, for generating a magnetic field in the thin steel strip; and
    a magnetic detection circuit for detection magnetic flux leakage occurring due to a defect in an interior or on the surface of the thin steel strip;
    wherein said magnetic detection circuit comprises:
        an oversaturation type magnetic sensor housed in said hollow roller, said magnetic sensor including a detection coil applied around a ferromagnetic core, said detection coil having two terminals;
        excitation power supply means for exciting said magnetic sensor to an oversaturation range by supplying an AC power to said detection coil of said magnetic sensor through a stationary impedance, said excitation power supply means comprising a pulse voltage generator for supplying positive and negative pulse voltages to said detection coil so as to generate a voltage across said two terminals of said detection coil;
        voltage detecting means coupled to said detection coil for detection positive and negative values of said voltage generated across said two terminals of said detection coil, said voltage detecting means comprising a pair of peak value detection circuits connected to one of said two terminals of said detection coil for respectively detecting said positive and negative peak values of said voltage generated across said two terminals of said detection coil; and
        arithmetic means for adding the positive and negative values that are detected by said voltage detecting means, and for determining the sum as a measured value corresponding to the magnetic flux leakage.

2. A magnetic inspection apparatus for a thin steel strip according to claim 1, wherein the pulse widths of said positive and negative pulse voltages are set to be 0.01 to 0.1 times pulse cycles thereof.

3. A magnetic inspection apparatus for a thin steel strip according to claim 1, further comprising direct current bias adding means for adding a DC bias voltage to the pulse voltages supplied by said pulse voltage generator to said detection coil, and bias control means for variably controlling said DC bias voltage in accordance with the measured value determined by said arithmetic means.

* * * * *